(12) United States Patent
Brady et al.

(10) Patent No.: US 11,053,065 B2
(45) Date of Patent: Jul. 6, 2021

(54) TABLET AND CAPSULE DISPENSING ASSEMBLY

(71) Applicant: Pill Development Group, LLC, Sarasota, FL (US)

(72) Inventors: Robert Owen Brady, Sarasota, FL (US); Joseph B. Bujalski, Advance, NC (US); Jeffery S. Heitzenrater, Spencerport, NY (US); Matthew William Vergin, St. Petersburg, FL (US); Jon Colin Leonard, Ave Maria, FL (US); Joel Raymond Chartier, Bradenton, FL (US)

(73) Assignee: Pill Development Group, LLC, Sarasota, FL (US)

( * ) Notice: Subject to any disclaimer, the term of this patent is extended or adjusted under 35 U.S.C. 154(b) by 134 days.

(21) Appl. No.: 16/204,276

(22) Filed: Nov. 29, 2018

(65) Prior Publication Data

US 2019/0091107 A1    Mar. 28, 2019

Related U.S. Application Data

(63) Continuation-in-part of application No. 16/161,965, filed on Oct. 16, 2018, now Pat. No. 10,772,805,
(Continued)

(51) Int. Cl.
*B65D 83/04* (2006.01)
*G16H 20/13* (2018.01)
(Continued)

(52) U.S. Cl.
CPC .......... *B65D 83/0409* (2013.01); *A61J 1/035* (2013.01); *A61J 7/0481* (2013.01); *G16H 20/13* (2018.01);
(Continued)

(58) Field of Classification Search
CPC ...... A61J 7/0418; A61J 7/0445; A61J 7/0076; A61J 7/0481; A61J 2200/30;
(Continued)

(56) References Cited

U.S. PATENT DOCUMENTS 4,572,403 A * 2/1986 Benaroya .................. A61J 7/04
                                                              221/15
4,785,969 A    11/1988 McLaughlin
(Continued)

FOREIGN PATENT DOCUMENTS

GB    1277163    6/1972

*Primary Examiner* — Rakesh Kumar
(74) *Attorney, Agent, or Firm* — Simpson & Simpson, PLLC; Michael Nicholas Vranjes

(57) ABSTRACT

A dispensing assembly, including a case including at least one aperture, a drive gear operatively arranged to engage the case, a tablet disc rotatably arranged in the case and including a plurality of compartments, and an electronics assembly, including a motor engaged with the drive gear, and a housing operatively arranged to engage the tablet disc, wherein the motor is arranged to rotate the electronics assembly and the tablet disc with respect to the case to align the plurality of compartments with the at least one aperture.

18 Claims, 28 Drawing Sheets

Related U.S. Application Data which is a continuation of application No. PCT/US2017/069049, filed on Dec. 29, 2017.

(60) Provisional application No. 62/440,569, filed on Dec. 30, 2016.

(51) Int. Cl.
*A61J 7/04* (2006.01)
*A61J 1/03* (2006.01)
*A61J 7/00* (2006.01)

(52) U.S. Cl.
CPC ............ *A61J 7/0076* (2013.01); *A61J 7/0418* (2015.05); *A61J 7/0445* (2015.05); *A61J 2200/30* (2013.01)

(58) Field of Classification Search
CPC .... A61J 2200/70; A61J 2205/60; A61J 1/035; B65D 83/0409; A61B 5/117; A61B 5/0022; A61B 5/024; A61B 5/7264; A61B 2562/0219; G16H 40/67; G16H 40/63; G16H 20/13; G06F 15/76; G07F 11/00
USPC ................................. 700/237; 221/25, 88, 15
See application file for complete search history.

(56) References Cited

U.S. PATENT DOCUMENTS

| | | | |
|---|---|---|---|
| 5,522,525 A * | 6/1996 | McLaughlin | A61J 7/0481 221/4 |
| 5,564,593 A * | 10/1996 | East, Sr. | A61J 7/0481 221/121 |
| 5,570,810 A * | 11/1996 | Lambelet, Jr. | B65D 83/0463 221/86 |
| 5,775,536 A | 7/1998 | Lambelet, Jr. et al. | |
| 5,799,821 A * | 9/1998 | Lambelet, Jr. | B65D 83/0454 221/5 |
| 5,915,589 A | 6/1999 | Lim | |
| 5,921,395 A * | 7/1999 | Alexander | B65D 83/0454 206/538 |
| 6,021,918 A | 2/2000 | Dumont et al. | |
| 6,098,835 A | 8/2000 | DeJonge | |
| 6,145,697 A * | 11/2000 | Gudish | A61J 7/0481 221/3 |
| 6,325,241 B1 * | 12/2001 | Garde | B65D 83/0454 206/533 |
| 6,601,729 B1 * | 8/2003 | Papp | A61J 7/0084 206/528 |
| 6,651,840 B1 * | 11/2003 | Van Dullemen | B65B 69/0058 221/88 |
| 6,669,022 B2 * | 12/2003 | Donegan | A61J 7/0076 206/531 |
| 6,702,146 B2 * | 3/2004 | Varis | A61J 7/0481 221/3 |
| 6,848,593 B2 * | 2/2005 | Papp | A61J 7/0084 221/197 |
| 6,988,634 B2 * | 1/2006 | Varis | A61J 7/0481 221/7 |
| 7,366,675 B1 | 4/2008 | Walker et al. | |
| 7,444,203 B2 | 10/2008 | Rosenblum | |
| 7,471,993 B2 | 12/2008 | Rosenblum | |
| 7,661,532 B2 | 2/2010 | Conley et al. | |
| 7,774,097 B2 | 8/2010 | Rosenblum | |
| 7,801,745 B2 | 9/2010 | Walker et al. | |
| 7,896,192 B2 * | 3/2011 | Conley | G07F 17/0092 221/15 |
| 7,978,564 B2 | 7/2011 | De La Huerga | |
| 8,033,424 B2 | 10/2011 | Rosenblum | |
| 8,069,056 B2 | 11/2011 | Walker et al. | |
| 8,286,821 B2 | 10/2012 | Mejia et al. | |
| 8,303,500 B2 | 11/2012 | Raheman | |
| 8,543,417 B1 | 9/2013 | Jackson | |
| 8,622,241 B2 | 1/2014 | Geboers et al. | |
| 8,636,172 B2 | 1/2014 | Dunn | |
| 8,725,291 B2 | 5/2014 | Czaja et al. | |
| 8,744,619 B2 | 6/2014 | Rosenblum | |
| 8,751,039 B1 | 6/2014 | Macoviak et al. | |
| 9,027,787 B2 * | 5/2015 | Eriksson | B65D 83/0454 221/83 |
| 9,135,790 B2 | 9/2015 | Wollin | |
| 9,218,458 B2 | 12/2015 | Baarman et al. | |
| 9,283,150 B2 | 3/2016 | Bujalski et al. | |
| 9,361,461 B2 | 6/2016 | Fauci | |
| 9,456,959 B2 * | 10/2016 | Reddy | A61J 7/0481 |
| 9,463,140 B2 * | 10/2016 | Reddy | B65D 83/0409 |
| 10,292,906 B1 * | 5/2019 | Gershoni | A61J 7/0427 |
| 10,470,976 B2 * | 11/2019 | Warden | A61J 1/18 |
| 2002/0026330 A1 | 2/2002 | Klein | |
| 2003/0050731 A1 | 3/2003 | Rosenblum | |
| 2003/0086338 A1 | 5/2003 | Sastry et al. | |
| 2003/0127463 A1 * | 7/2003 | Varis | A61J 7/0481 221/2 |
| 2003/0174554 A1 | 9/2003 | Dunstone et al. | |
| 2003/0183226 A1 | 10/2003 | Brand et al. | |
| 2003/0209558 A1 | 11/2003 | Cross | |
| 2004/0099561 A1 * | 5/2004 | Christensen | B65D 83/0454 206/461 |
| 2004/0172163 A1 | 9/2004 | Varis | |
| 2004/0215369 A1 | 10/2004 | Rosenblum | |
| 2005/0049746 A1 | 3/2005 | Rosenblum | |
| 2006/0144846 A1 * | 7/2006 | Varis | G07F 11/50 221/2 |
| 2006/0180600 A1 | 8/2006 | Talyor | |
| 2006/0218014 A1 | 9/2006 | Walker et al. | |
| 2006/0218015 A1 | 9/2006 | Walker et al. | |
| 2007/0073560 A1 | 3/2007 | Walker et al. | |
| 2007/0156282 A1 | 7/2007 | Dunn | |
| 2007/0163583 A1 | 7/2007 | Brand et al. | |
| 2007/0260491 A1 | 11/2007 | Palmer et al. | |
| 2007/0271001 A1 | 11/2007 | Ratnakar | |
| 2007/0293982 A1 | 12/2007 | Rosenblum | |
| 2008/0030309 A1 | 2/2008 | Darrouzet | |
| 2008/0077440 A1 | 3/2008 | Doron | |
| 2008/0203107 A1 * | 8/2008 | Conley | G07F 11/16 221/1 |
| 2008/0210701 A1 | 9/2008 | Cooper | |
| 2008/0283542 A1 | 11/2008 | Lanka et al. | |
| 2009/0048712 A1 | 2/2009 | Rosenblum | |
| 2009/0164238 A1 | 6/2009 | Auchinleck | |
| 2009/0294521 A1 | 12/2009 | de la Huerga | |
| 2010/0100237 A1 | 4/2010 | Ratnakar | |
| 2010/0228141 A1 | 9/2010 | Kountotsis | |
| 2010/0305750 A1 * | 12/2010 | Conley | A61J 7/0427 700/237 |
| 2010/0318218 A1 | 12/2010 | Muncy, Jr. et al. | |
| 2010/0324728 A1 | 12/2010 | Rosenblum | |
| 2011/0036803 A1 | 2/2011 | Mejia et al. | |
| 2011/0060457 A1 | 3/2011 | De Vrught et al. | |
| 2011/0125317 A1 | 5/2011 | Dunn | |
| 2011/0125318 A1 | 5/2011 | Dunn | |
| 2011/0166700 A1 | 7/2011 | Dunn | |
| 2011/0247663 A1 * | 10/2011 | Gadini | A47L 15/4463 134/115 R |
| 2011/0270442 A1 | 11/2011 | Conley et al. | |
| 2012/0003928 A1 | 1/2012 | Geboers et al. | |
| 2012/0006700 A1 | 1/2012 | Geboers et al. | |
| 2012/0065776 A1 | 3/2012 | Czaja et al. | |
| 2012/0089249 A1 | 4/2012 | Rosenblum | |
| 2012/0101630 A1 | 4/2012 | Daya et al. | |
| 2012/0165975 A1 | 6/2012 | Yi et al. | |
| 2013/0088328 A1 | 4/2013 | DiMartino et al. | |
| 2013/0090594 A1 | 4/2013 | Palmer et al. | |
| 2013/0110283 A1 | 5/2013 | Baarman et al. | |
| 2013/0134180 A1 | 5/2013 | Cheyene | |
| 2013/0166066 A1 | 6/2013 | Dunn | |
| 2013/0197693 A1 | 8/2013 | Kamen et al. | |
| 2013/0256331 A1 | 10/2013 | Giraud et al. | |
| 2013/0261794 A1 | 10/2013 | Fauci | |
| 2013/0304255 A1 | 11/2013 | Ratnakar | |
| 2013/0317645 A1 | 11/2013 | Daya et al. | |
| 2014/0052468 A1 | 2/2014 | Burrows et al. | |
| 2014/0058559 A1 | 2/2014 | Haynes | |

(56) References Cited

U.S. PATENT DOCUMENTS

| | | |
|---|---|---|
| 2014/0207278 A1 | 7/2014 | Czaja et al. |
| 2014/0214200 A1 | 7/2014 | Chrusciel et al. |
| 2014/0239062 A1 | 8/2014 | Nurse et al. |
| 2014/0244031 A1 | 8/2014 | Macoviak et al. |
| 2014/0263425 A1 | 9/2014 | Akdogan et al. |
| 2014/0277705 A1 | 9/2014 | Czaja et al. |
| 2014/0277707 A1 | 9/2014 | Akdogan et al. |
| 2014/0324216 A1 | 10/2014 | Beg et al. |
| 2014/0326744 A1 | 11/2014 | Ratnakar |
| 2014/0339248 A1 | 11/2014 | Reddy et al. |
| 2014/0339249 A1 | 11/2014 | Reddy et al. |
| 2014/0346186 A1 | 11/2014 | Reddy et al. |
| 2014/0372144 A1 | 12/2014 | Sterns et al. |
| 2015/0025679 A1 | 1/2015 | Rosenblum |
| 2015/0048101 A1* | 2/2015 | Reddy ............... B65D 83/0409 221/1 |
| 2015/0061832 A1 | 3/2015 | Pavlovic et al. |
| 2015/0145672 A1 | 5/2015 | Chu |
| 2015/0148943 A1* | 5/2015 | Sullivan ............... A61J 7/0076 700/231 |
| 2015/0161558 A1 | 6/2015 | Gitchell et al. |
| 2015/0254427 A1 | 9/2015 | Burrows et al. |
| 2015/0272825 A1 | 10/2015 | Lim et al. |
| 2015/0294551 A1 | 10/2015 | Edwards et al. |
| 2015/0310185 A1 | 10/2015 | Shah |
| 2015/0310186 A1 | 10/2015 | Conley et al. |
| 2015/0317455 A1 | 11/2015 | Lemann et al. |
| 2015/0343144 A1 | 12/2015 | Altschul et al. |
| 2015/0360834 A1 | 12/2015 | Mikhail |
| 2016/0031620 A1 | 2/2016 | Rosenquist |
| 2016/0081882 A1 | 3/2016 | Joyce et al. |
| 2016/0085938 A1 | 3/2016 | Hans |
| 2016/0128906 A1* | 5/2016 | Baarman ............... G16H 20/13 221/2 |
| 2016/0158107 A1 | 6/2016 | Dvorak et al. |
| 2016/0203292 A1 | 7/2016 | Kamen et al. |
| 2016/0247345 A1 | 8/2016 | Ratnakar |
| 2018/0303718 A1* | 10/2018 | Song ..................... G07F 11/44 |
| 2018/0318173 A1* | 11/2018 | Paz ....................... A61J 7/0076 |
| 2019/0091107 A1* | 3/2019 | Brady ................... A61J 7/0445 |
| 2019/0201293 A1* | 7/2019 | Brady ................... A61J 7/0445 |
| 2019/0365607 A1* | 12/2019 | Kugler .................. A61J 1/035 |

* cited by examiner

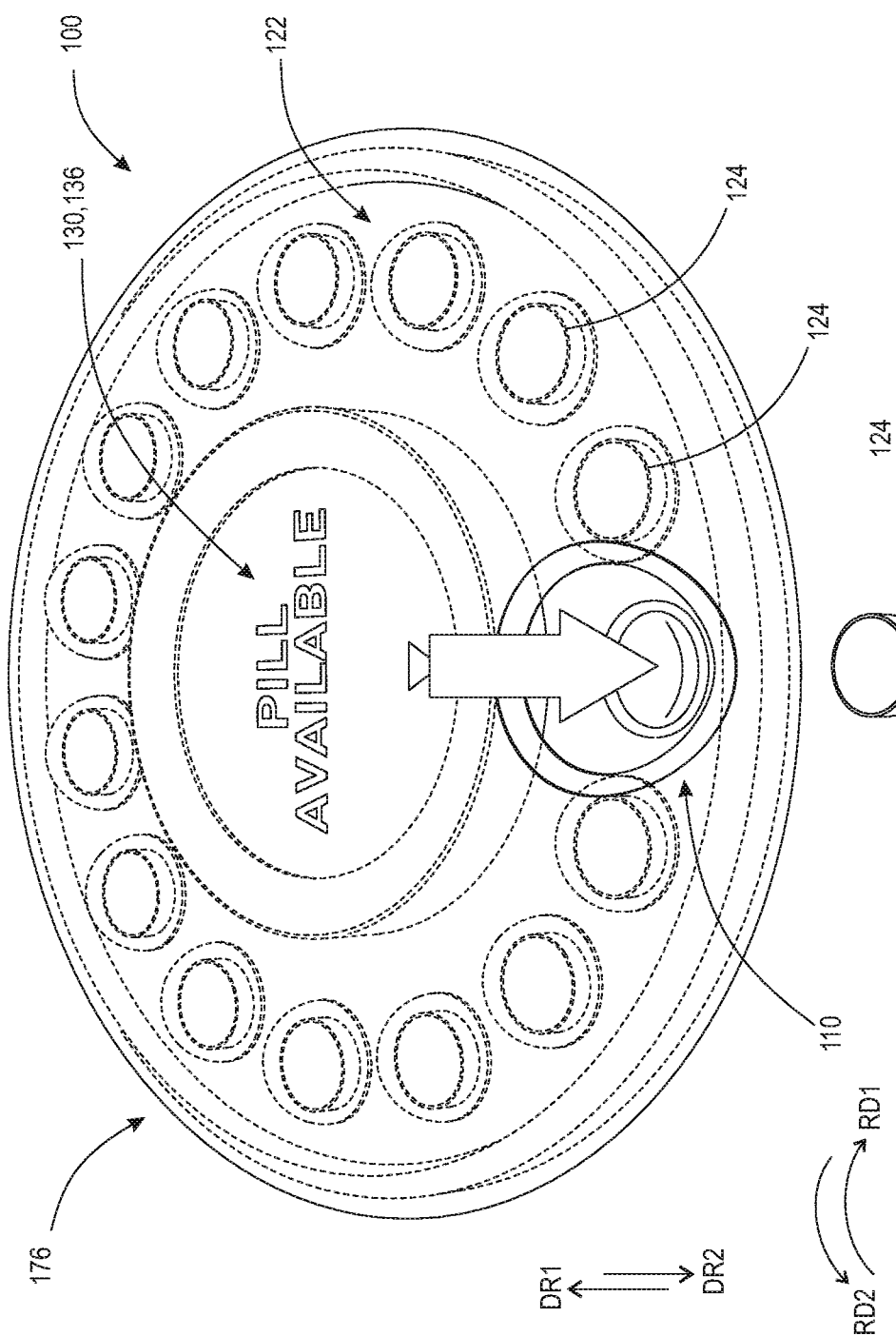

TABLET AND CAPSULE DISPENSING ASSEMBLY

CROSS-REFERENCE TO RELATED APPLICATIONS

This application is filed under 35 U.S.C. § 120 as a continuation-in-part of U.S. patent application Ser. No. 16/161,965, filed on Oct. 16, 2018, which application was filed under 35 U.S.C. §§ 111(a) and 365(c) as a continuation of International Patent Application No. PCT/US17/69049, filed Dec. 29, 2017, which application claims the benefit under 35 U.S.C. § 119(e) of U.S. Provisional Patent Application No. 62/440,569, filed on Dec. 30, 2016, which applications are herein incorporated by reference in their entireties.

FIELD

The disclosure relates to tablet and capsule dispensers, more particularly to tablet and capsule dispensers that dispense tablets and capsules in compliance with a predefined regimen specific to a time interval or schedule, and, even more specifically, to a tablet and capsule dispensers that prevent access to tablets and capsules except as specified by a pre-defined regimen.

BACKGROUND

Opioids are a type of medicine often used to help relieve pain. Opioids work by attaching themselves to specific proteins called opioid receptors, which are found in nerve cells in the brain, spinal cord, gastrointestinal tract, and other organs within the human body. When opioids attach to these receptors, they change how the brain perceives pain by creating feelings of pleasure and euphoria. The human brain is wired to record feelings of pleasure and euphoria, cuing the individual to take more and more of the drug. As a result, the user can become dependent on, and addicted to, opioids very quickly. Studies estimate that as many as 36 million users worldwide currently suffer from opioid addiction.

Opioid addiction soon leads to adverse health effects such as dizziness, nausea, aches and pains, tremors, chills, vomiting, and constipation. In addition to these negative health effects, the user builds a tolerance to the positive effects of the opioid, which can lead to overdose and death. In 2015, the Centers for Disease Control and Prevention reported that drug overdoses accounted for 52,504 deaths in the United States, 63.1% of which involved an opioid.

To better control potentially addictive prescription medications, these drugs are typically controlled in a closed system of distribution that seeks to oversee the importation, manufacture, distribution, and dispensing of controlled substances. This closed system is designed to provide a discrete chain of custody for controlled substances and to ensure that those substances are used in accordance with a prescribed manner which is specific to a given quantity of the substance taken at defined intervals of time. This closed system effectively opens when a controlled substance is released into the hands of the patient or end-user. The end-user, while bound by the laws of use specified by the closed system, is largely free to operate on the honor system and trusted to follow the regimen specified by the prescription instructions.

Several unintended consequences arise from this honor system. These include, but are not limited to, missed doses, overdoses, unused quantities of controlled substances, and access to controlled substances by unauthorized users. Further, well-meaning end-users often dispose of unused quantities of controlled substances into the wastewater supply where they contaminate water resources with unknown and poorly studied consequences.

In the case of addictive substances such as opioids, an attractive nuisance is created when unauthorized users gain access to and ingest prescription medication. For many, this first experience leads to a downward spiral of abuse which tragically, and all too often, results in addiction. These individuals may move to cheaper and more readily accessible street drugs like heroin in pursuit of that euphoric high they experienced when using opioids. Deaths related to heroin and opioid abuse continue to spiral out of control, due in part to the lack of control under the current honor system of managing the distribution of controlled substances to end-users.

U.S. Pat. No. 7,978,5464 (De La Huerga) discloses a device that relies upon an electronic processor and communication with the end-user to remind of the proper dose, track usage, and warn of drug interactions. It does not, however, physically limit access to controlled substances. A further disadvantage of the device in De La Huerga is that the device relies upon separate consoles, which would complicate adherence to regimens for end-users who are traveling or simply going about their daily lives.

U.S. Pat. No. 9,218,458 (Baarman) discloses another device that tracks usage, reminds and warns end-users by using an additional electronic device in proximity with the invention before dispensing controlled substances. While this device moves to physically limit access, it requires an outboard device for user validation. Further, the invention automatically dispenses controlled substances according to a pre-defined regimen. This feature may conflict with regimen instructions such as, "take as needed", or "take one or two tablets, as needed."

United States Patent Application Publication No. 2014/0214200 (Chrusciel) controls dispensing "several non-individually packaged pills at a plurality of times". The nature of providing for a "plurality of removable magazines" results in a device that is much larger than is conveniently portable and requires an end-user to move all of their controlled substances about as a single group. The use of rechargeable batteries charged from a wall outlet further restricts portability.

U.S. Pat. No. 8,622,241 (Geboers) describes a device where tablets or capsules are dispensed at preset intervals and quantities from columns of loose tablets, pills or capsules. The device is mechanical or electromechanical, but it requires an outboard unit containing a processor and communication device to track end-user behavior and to respond to flexible requirements embodied in many medication regimens.

U.S. Pat. No. 9,283,150 (Bujalski) describes a device that relies upon a mechanical timer to release controlled substances in accordance with a pre-defined regimen. End-users are alerted when the time interval is reached, but there is limited flexibility in managing instructions such as, "Take one or two tablets as needed". This invention lacks the ability to record and communicate a history of usage, the ability to display remaining dosages, or to determine the time until the next dosage.

Thus, there is a long-felt need for a tablet and capsule dispenser that prevents access to tablets and capsules except as specified by a pre-defined regimen and has the ability to record and communicate a history of usage, to display remaining dosages, to display the time until the next dosage, and to prevent early access to the next dosage.

SUMMARY

According to aspects illustrated herein, there is provided a dispensing assembly, comprising a case including at least one aperture, a drive gear operatively arranged to engage the case, a tablet disc rotatably arranged in the case and including a plurality of compartments, and an electronics assembly, including a motor engaged with the drive gear, and a housing operatively arranged to engage the tablet disc, wherein the motor is arranged to rotate the electronics assembly and the tablet disc with respect to the case to align the plurality of compartments with the at least one aperture.

According to aspects illustrated herein, there is provided a dispensing assembly for storing and dispensing medication in the form of pills, capsules, and tablets, the dispensing assembly comprising a case including a superior component, an inferior component non-rotatably connected to the superior component, a cavity formed between the superior component and inferior component, and at least one aperture, a drive gear arranged in the cavity and operatively arranged to engage at least one of the inferior component and the superior component, a tablet disc rotatably arranged in the cavity and including a plurality of compartments circumferentially arranged thereon, and an electronics assembly, including a housing operatively arranged to engage the tablet disc, and a motor non-rotatably connected to the housing and engaged with the drive gear, wherein the motor is arranged to rotate the electronics assembly and the tablet disc with respect to the case to align a compartment of the plurality of compartments with the at least one aperture.

According to aspects illustrated herein, there is provided a dispensing assembly for storing and dispensing medication, comprising a case including a cavity and at least one aperture, a tablet disc rotatably arranged in the cavity and having a plurality of compartments, an electronics assembly arranged to engage the tablet disc, the electronics assembly including a motor and a circuit board, wherein the circuit board includes a timer operatively arranged to activate the motor at a predetermined time and angularly displace the tablet disc with respect to the case, and a sensor operatively arranged to deactivate the motor when a displaced angular distance of the tablet disc is equal to a predetermined angular distance.

According to aspects illustrated herein, there is provided a tablet and capsule dispensing assembly, comprising a case including an inner circumferential surface having a first plurality of teeth a tablet disc having a plurality of tablets disposed circumferentially thereon, the tablet disc arranged to rotate about a central axis and within the case, and a lock arranged to engage with the first plurality of teeth to prevent rotation of the tablet disc in a first rotational direction during a first predetermined time interval.

According to aspects illustrated herein, there is provided a tablet and capsule dispensing assembly, comprising a case including a superior component having a first aperture, and an inferior component arranged to engage with the superior component forming a first cavity therebetween, the inferior component having a second aperture, a tablet disc having a plurality of tablets disposed circumferentially thereon, the tablet disc arranged to rotate within the case, wherein the first aperture and the second aperture are arranged to, when aligned, allow a first tablet of the plurality of tablets to be removed from the tablet disc, and a lock arranged to prevent rotation of the tablet disc in a first rotational direction during a first predetermined time interval.

According to aspects illustrated herein, there is provided a tablet and capsule dispensing assembly including a case, the case having an inner circumferential surface, the inner circumferential surface having a first plurality of teeth, a tablet disc having a plurality of tablets disposed about a circumference of the tablet disc, the tablet disc arranged to rotate about a central axis and within the case, and a lock arranged to engage with the first plurality of teeth to prevent rotation of the tablet disc in a first rotational direction at a first predetermined time interval.

According to aspects illustrated herein, there is provided a tablet and capsule dispensing assembly, including a case having a superior component and an inferior component operatively arranged to form a first cavity therebetween, a tablet disc arranged within the first cavity, the tablet disc having a plurality of tablets disposed about a circumference of the tablet disc, and arranged to rotate about a central axis and within the case, and a lock arranged to prevent rotation of the tablet disc in a first rotational direction at a first predetermined time interval. The lock further includes a first component and a second component. The first component including a display and a first circuit electrically connected to the display. The second component including a solenoid actuator, a pivotable catch, a second plurality of teeth disposed on an outer circumferential surface of the second component, and a ratchet operatively arranged to engage with the second plurality of teeth and the case.

These and other objects, features, and advantages of the present disclosure will become readily apparent upon a review of the following detailed description of the disclosure, in view of the drawings and appended claims.

BRIEF DESCRIPTION OF THE DRAWINGS

Various embodiments are disclosed, by way of example only, with reference to the accompanying schematic drawings in which corresponding reference symbols indicate corresponding parts, in which:

FIG. 4A is a front perspective view of the top of the dispensing assembly;

DETAILED DESCRIPTION

Figure 1A:
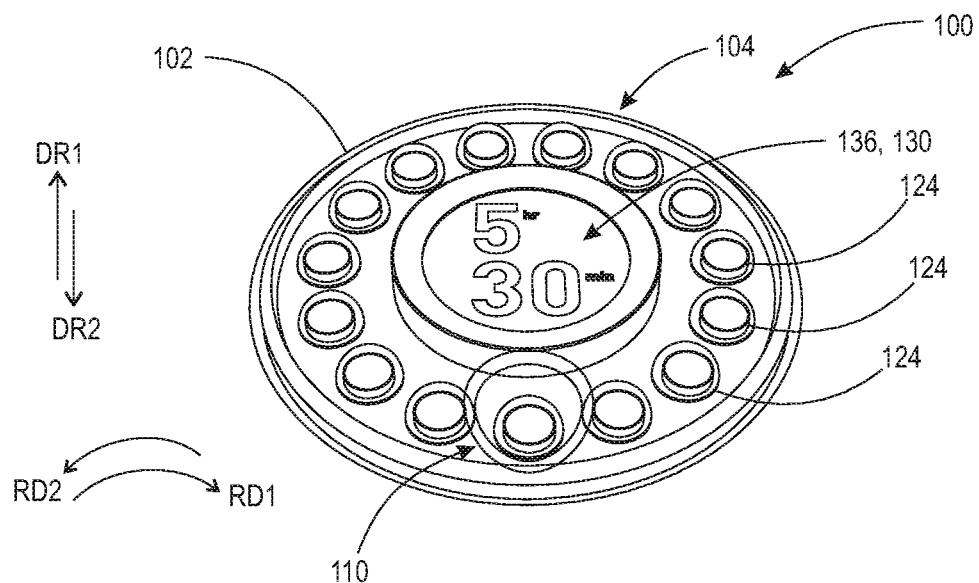
FIG. 1A is a front perspective view of the top of a dispensing assembly.
Figure 1B:
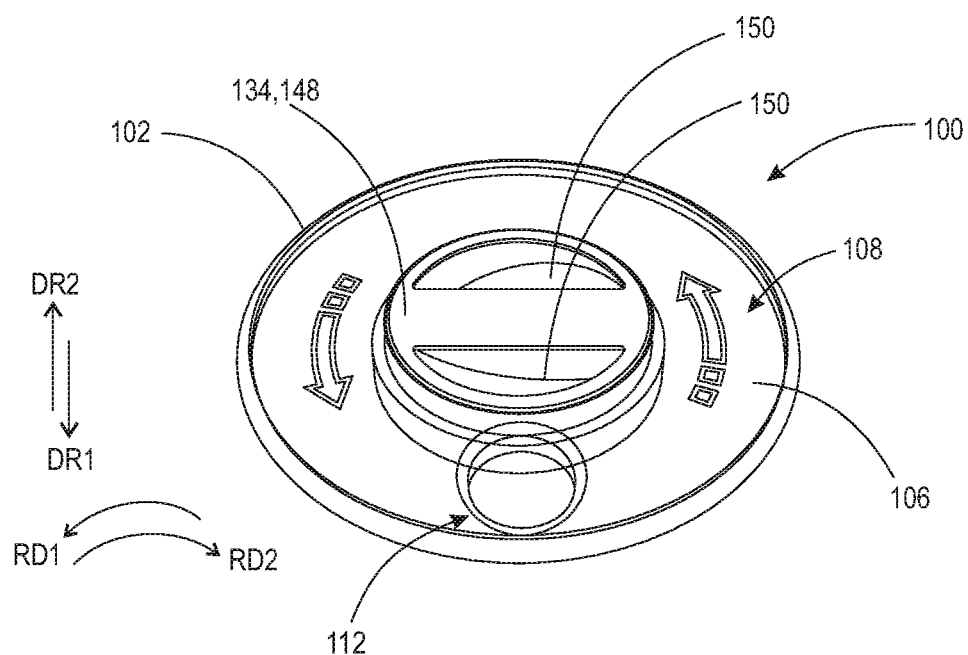
FIG. 1B is a front perspective view of the bottom of the dispensing assembly shown in FIG. 1A.

At the outset, it should be appreciated that like drawing numbers on different drawing views identify identical, or functionally similar, structural elements. It is to be understood that the claims are not limited to the disclosed aspects.

Furthermore, it is understood that this disclosure is not limited to the particular methodology, materials and modifications described and as such may, of course, vary. It is also understood that the terminology used herein is for the purpose of describing particular aspects only, and is not intended to limit the scope of the claims.

Unless defined otherwise, all technical and scientific terms used herein have the same meaning as commonly understood to one of ordinary skill in the art to which this disclosure pertains. It should be understood that any methods, devices or materials similar or equivalent to those described herein can be used in the practice or testing of the example embodiments. The assembly of the present disclosure could be driven by hydraulics, electronics, pneumatics, and/or springs.

It should be appreciated that the term "substantially" is synonymous with terms such as "nearly," "very nearly," "about," "approximately," "around," "bordering on," "close to," "essentially," "in the neighborhood of," "in the vicinity of," etc., and such terms may be used interchangeably as appearing in the specification and claims. It should be appreciated that the term "proximate" is synonymous with terms such as "nearby," "close," "adjacent," "neighboring," "immediate," "adjoining," etc., and such terms may be used interchangeably as appearing in the specification and claims. The term "approximately" is intended to mean values within ten percent of the specified value.

By "non-rotatably connected" or "non-rotatably secured" elements, we mean that: the elements are connected so that whenever one of the elements rotate, all the elements rotate; and relative rotation between the elements is not possible. Radial and/or axial movement of non-rotatably connected elements with respect to each other is possible, but not required. By "rotatably connected" elements, we mean that the elements are rotatable with respect to each other.

Moreover, as used herein, "and/or" is intended to mean a grammatical conjunction used to indicate that one or more of the elements or conditions recited may be included or occur. For example, a device comprising a first element, a second element and/or a third element, is intended to be construed as any one of the following structural arrangements: a device comprising a first element; a device comprising a second element; a device comprising a third element; a device comprising a first element and a second element; a device comprising a first element and a third element; a device comprising a first element, a second element and a third element; or, a device comprising a second element and a third element.

The term "superior component" as used in the present disclosure is intended to mean the component of the case located in the highest position relative to the inferior component component in first direction DR1.

The term "inferior component" as used in the present disclosure is intended to mean the component of the case located in the lowest position relative to the superior component in first direction DR1.

Adverting now to the figures, FIGS. 1A-2B illustrate various perspective views of dispensing assembly 100 in an assembled state and an exploded state. Dispensing assembly 100 includes case 102 which is substantially toroidal in shape. Case 102 includes superior component 104 and inferior component 106. Superior component 104 and inferior component 106 are arranged to engage via a press-fit, friction-fit, or interference-fit, leaving a substantially toroidal first cavity 108 therebetween. It is intended that superior component 104 and inferior component 106 are arranged such that once they are fitted together, no user can open the case, i.e., only a manufacturer or healthcare professional may separate the components. In some embodiments, superior component 104 and inferior component 106 are made of high impact modified Poly(methyl methacrylate) (PMMA); however, it should be appreciated that any other durable material can be used, e.g., high-density polyethylene, low-density polyethylene, metal, high-impact polystyrene, Polycarbonate (PC), Polyether Imide (PEI), or any other material which can resist breaking or cracking while in use, and prevent tampering and/or render evident any tampering caused by the user. Superior component 104 further includes aperture 110, and inferior component 106 further includes aperture 112. Apertures 110 and 112 are arranged such that when case 102 is assembled, aperture 110 of superior component 104 is aligned with, and directly above, aperture 112 of inferior component 106. Superior component also includes first rim 114 (shown in FIG. 2B) which contains first plurality of teeth 116 disposed about a circumferential surface of first rim 114 and operatively arranged to engage with pivotable catch 152 discussed infra. Inferior component 106 further comprises opening 118 operatively arranged to receive second component 134 of lock 130 discussed infra; and, second rim 120 (shown in FIG. 2A) arranged to engage with lock 130 discussed infra.

Dispensing assembly 100 further comprises tablet disc 122. Tablet disc 122 and lock 130 (discussed infra) are positioned within first cavity 108 of case 102 when dispensing assembly 100 is completely assembled. Tablet disc 122 further comprises plurality of tablets 124 disposed about the circumference of tablet disc 122. The plurality of tablets 124 are set apart from each other a fixed circumferential distance such that they are evenly spaced. In some embodiments, tablet disc 122 is a prefabricated blister pack with a plurality of individual cells which isolate a single dose of a particular medication, i.e., each tablet is intended to be a single dose of a particular medication. The distance between each tablet or cell and the size of apertures 110 and 112 are proportional such that access to tablets is limited to one tablet at a time through apertures 110 and 112. Tablet disc 122 further comprises first through-bore 126 arranged to engage with first projection 140 (discussed infra) and at least one second through-bore 128 arranged to engage with at least one second projection 146 (not shown and discussed infra).

Dispensing assembly 100 further comprises lock 130. Lock 130 comprises first component 132 and second component 134. First component 132 comprises display 136, and first circuit 138 (shown in FIG. 3). In some embodiments, display 136 is an E-ink display; however, it should be appreciated that other displays are possible, e.g., a touch-screen display, an Light-Emitting Diode (LED) display, an Electroluminescent (ELD) display, a Plasma Display Panel (PDP) display, an Organic Light-Emitting Diode (OLED) display, a Liquid Crystal (LCD) display, or other equivalent displays. Display 136 is arranged to show the current state of dispensing assembly 100 and the time interval remaining until tablet disc 122 can be rotated to the next position (description of use of the assembly described infra). Second component 134 comprises, first projection 140 having first surface 142, second cavity 144, at least one second projection 146 (not shown), second surface 148 having a plurality of grips 150, solenoid actuator 152, pivotable catch 154, second plurality of teeth 156, and ratchet 158.

First projection 140 is a substantially cylindrical protrusion arranged to be concentric with second component 134 and further comprises second plurality of teeth 156. Second plurality of teeth 156 are operatively arranged on the outer circumference of first projection 140 and arranged to engage with ratchet 158. First projection 140 further includes first surface 142. First surface 142 comprises at least one second projection 146 (not shown) and second cavity 144. At least one second projection 146 is a peg or other projection operatively arranged to protrude in first direction DR1 with respect to first surface 142 and engage with through-bores 128 of tablet disc 122. When completely assembled, first projection 140 and at least one second projection 146 slide within, and engage with, first through-bore 126 and at least one second through-bore 128 of tablet disc 122, respectively. Second cavity 144 is arranged to receive solenoid actuator 152 when dispensing assembly 100 is fully assembled. Second surface 148, which is arranged opposite first surface 142 on second component 134, includes plurality of grips 150. Plurality of grips 150 are illustrated as two quadraspherical (one quarter of a sphere) cavities separated by a portion of second component 134; however, it should be appreciated that any physical arrangement that allows for a user to provide sufficient torque on lock 130 to rotate second component 134 relative to first component 132 can be used. Plurality of grips 150 are arranged such that a user can grip and provide a rotational force in first rotational direction RD1 or second rotational direction RD2 when a new tablet/pill is needed.

Figure 2A:
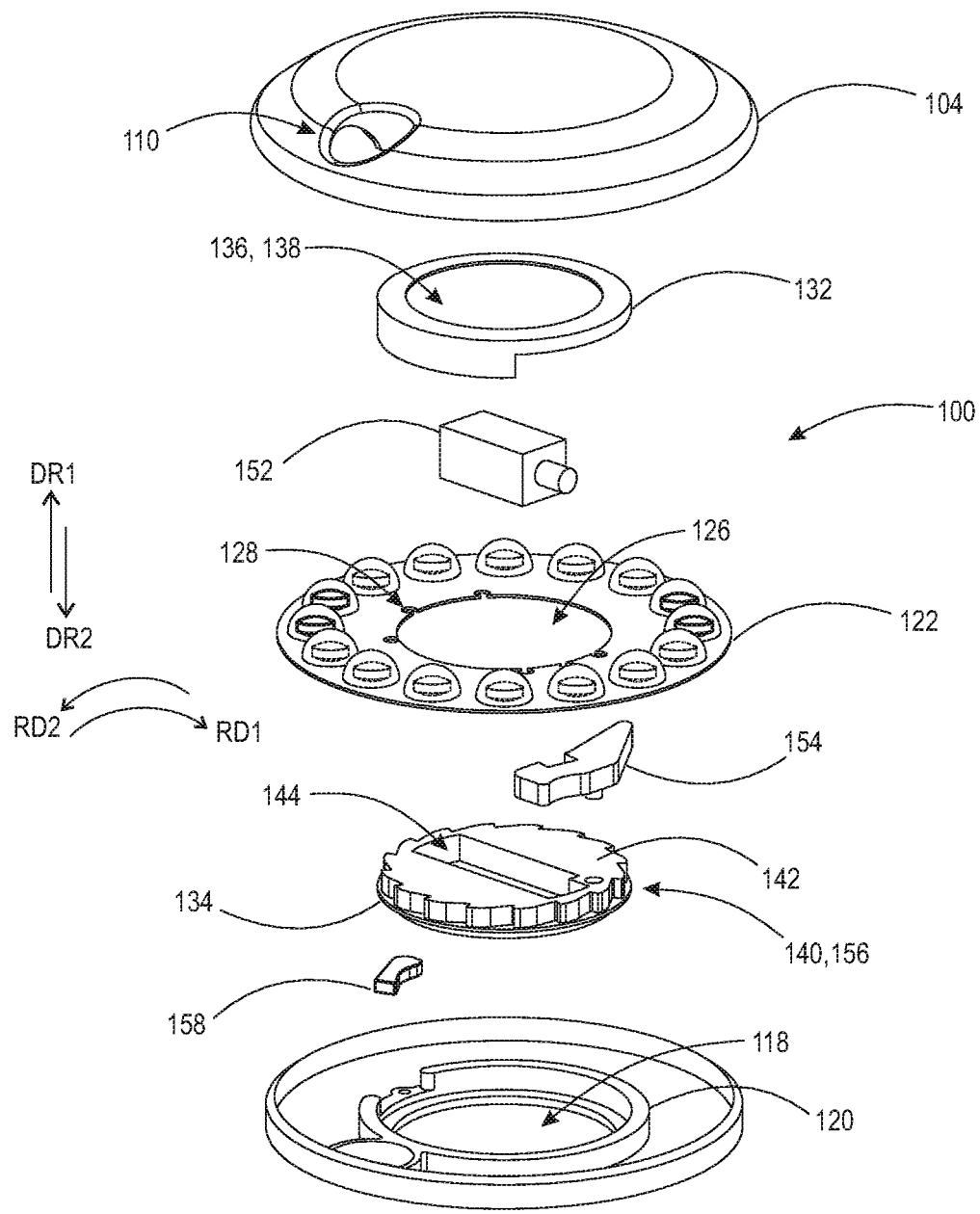
FIG. 2A is a front perspective exploded view of the dispensing assembly of FIG. 1A.
Figure 2B:
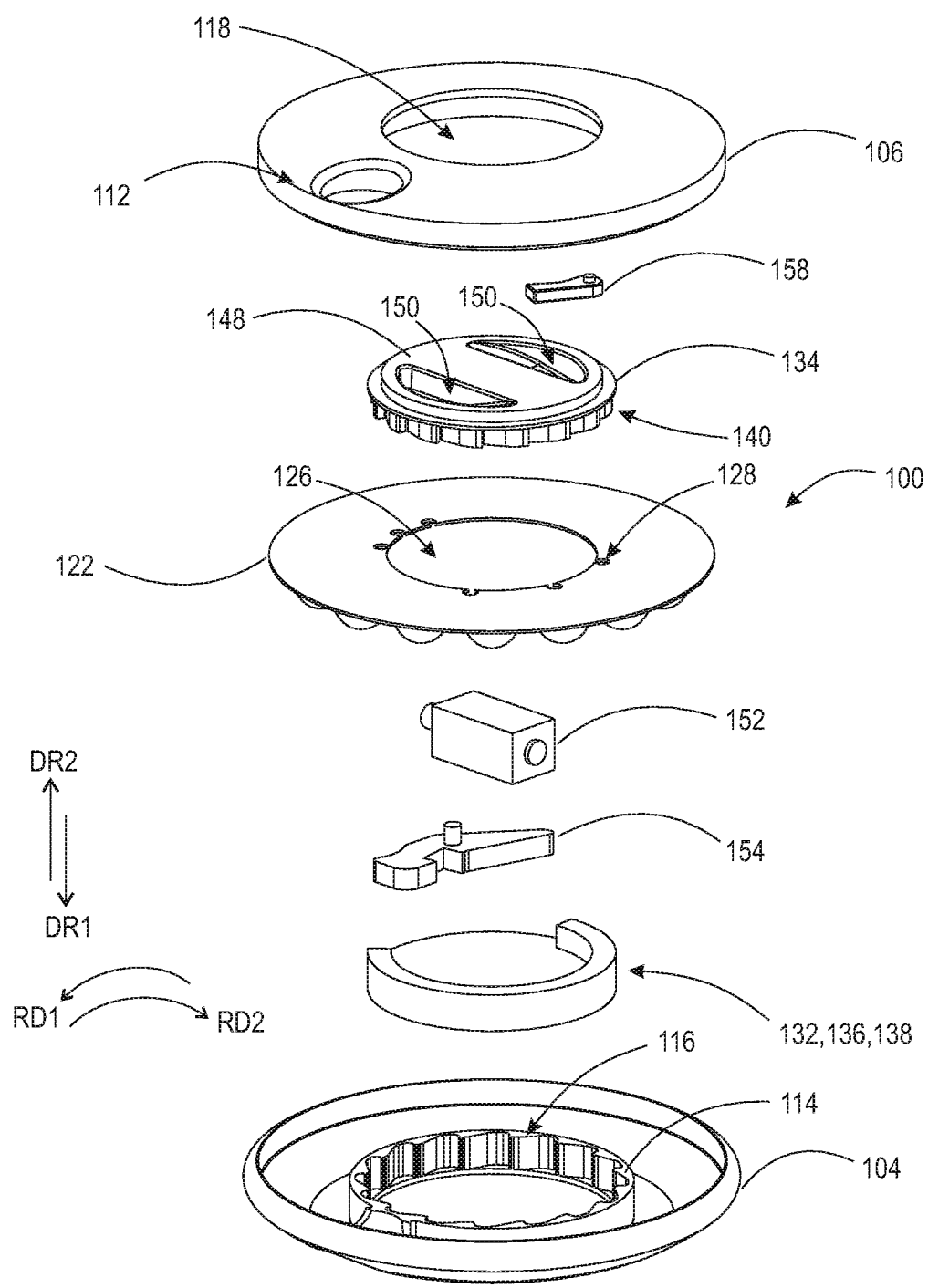
FIG. 2B is a front perspective exploded view of the dispensing assembly of FIG. 1B.
Figure 8:
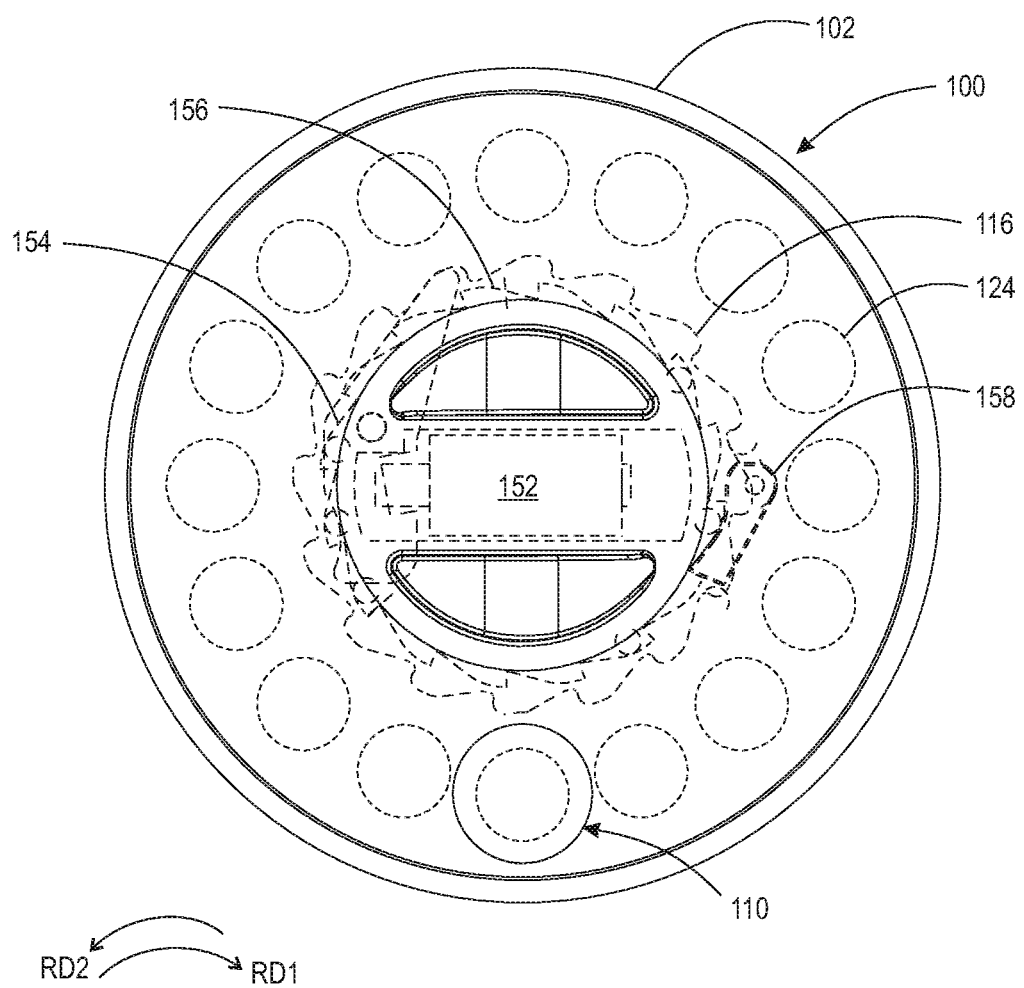
FIG. 8 is top plan view of a dispensing assembly.

It should be appreciated that first plurality of teeth 116 and second plurality of teeth 156 can be angled such that they prevent rotational motion of tablet disc 122 in either first rotational direction RD1 or second rotational direction RD2. For example, FIGS. 1A, 1B, and 4A-5C illustrate arrangements where ratchet 158 prevents rotational motion in rotational direction RD2 and pivotable catch 154 prevents and/or allows for rotational motion of tablet disc 122 in first rotational direction RD1. However, it should be appreciated that, as shown in FIGS. 2A, 2B and 8, first plurality of teeth 116 and second plurality of teeth 156 can be angled such that ratchet 158 prevents rotational motion of tablet disc 122 in first rotational direction RD1 and pivotable catch 154 prevents and/or allows for rotational motion of tablet disc 122 in second rotational direction RD2.

Solenoid actuator 152 is operatively arranged to sit within second cavity 144 and engage with pivotable catch 154 causing pivotable catch 154 to pivot and engage and/or disengage with first plurality of teeth 116 of superior component 104. As illustrated in FIGS. 1A, 1B, and 4A-5C, when solenoid actuator 152 is disengaged, tablet disc 122 is prevented from rotating in a first rotational direction RD1 and second rotational direction RD2. When solenoid actuator 152 is engaged, i.e., extended, tablet disc 122 is free to rotate in first rotational direction RD1. It should be appreciated that any actuator known in the art can be used to engage with first plurality of teeth 116. Pivotable catch 154 has a peg which rotatably engages with a partial through-bore disposed within first surface 142 of second component 134 such that it can pivot when engaged with solenoid actuator 152. First plurality of teeth 116 and pivotable catch 154 are arranged such that they are not affected by vibrations or gyrations which could be experienced in the average use of the assembly.

It should be appreciated that second component 134 is operatively arranged to sit within, and rotate independently from, first component 132. First component 132 is intended to remain non-rotatably secured to superior component 104 such that, when tablet disc 124 and second component 134 rotate in second rotational direction RD2, first component 132, which contains display 136, remains rotationally locked in case 102. This ensures that the display is always visible from the side of dispensing assembly 100 that comprises apertures 110 and 112. Additionally, as solenoid actuator 152 must be permitted to rotate with second component 134 while simultaneously maintaining electronic communication with first circuit 138, solenoid actuator 152 can be electrically connected to first circuit 138 with any wired or wireless circuit capable of transferring electricity to a rotating body, e.g., electrical slip rings, pancake slip rings, wireless slip rings, wireless power transfer circuits, inductive power transfer circuits, etc.

Figure 3:
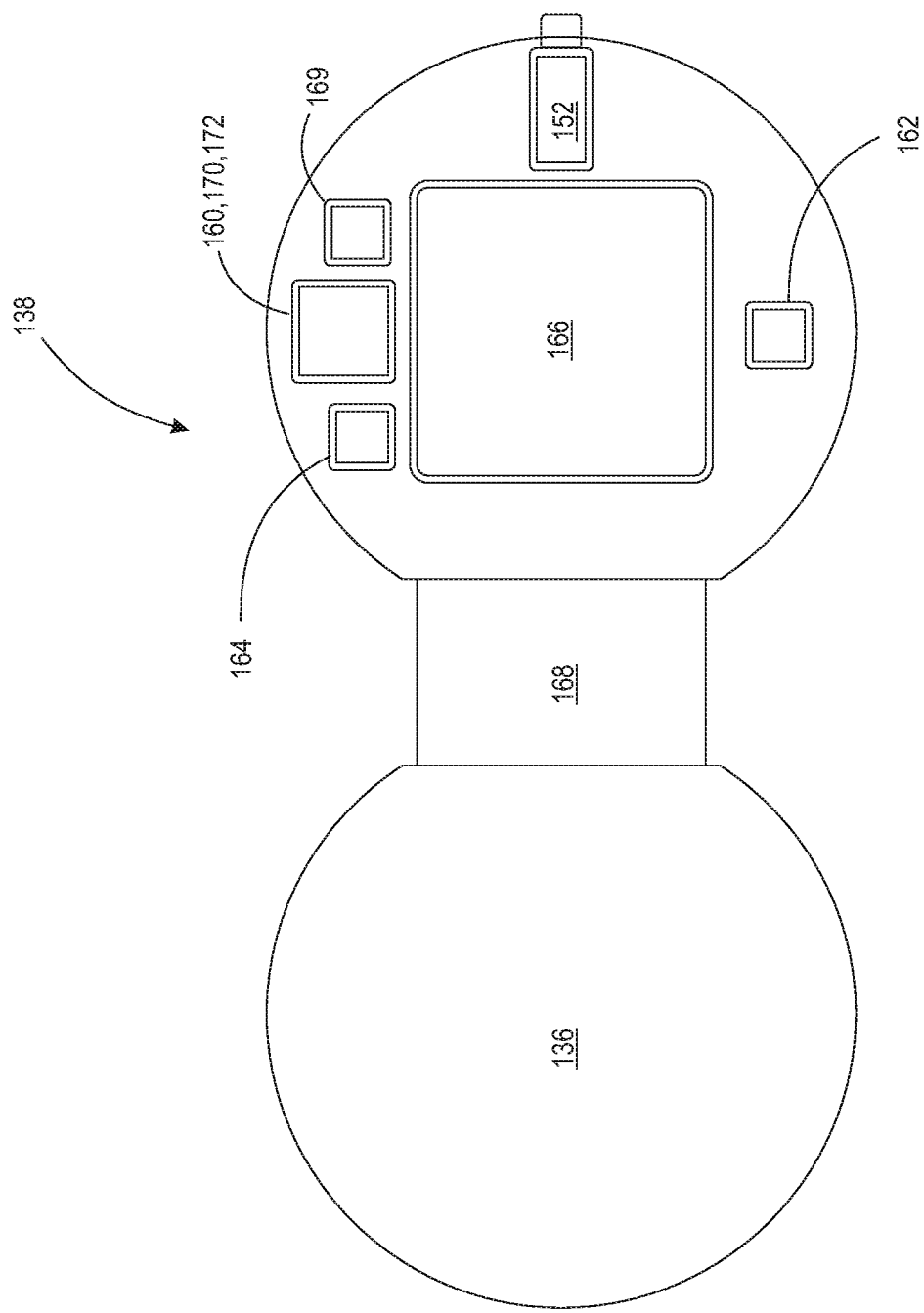
FIG. 3 is a high-level schematic view of a circuit associated with a dispensing assembly.

FIG. 3 illustrates a high-level schematic view of first circuit 138. First circuit 138 comprises microcontroller 160, timer 162, antenna 164, power supply 166, and flex circuit 168, and sensor 169. Microcontroller 160 further includes processor 170 and memory 172, which are operatively arranged to store and execute a set of non-transitory computer readable instructions. Memory 172 can store a first data set comprised of at least one date, at least one time, a rotational position of the tablet disc, and an integer. The date, time, and integer can reflect the history of a user's interaction with dispensing assembly 100 and keep track of which pill/tablet was accessed at what time. In some embodiments, microcontroller 160 is a Cypress Semiconductor part no.: CY8C4247LQI-BL483 available from Mouser Electronics; however, it should be appreciated that any other suitable microcontroller could be used to store the set of non-transitory computer readable instructions and first data set.

Timer 162 is a simple circuit operatively arranged to provide a base time signal to a microcontroller. This circuit comprises, for example, a crystal quartz oscillator. In some embodiments, timer 162 is a crystal oscillator part no.: ECS-240-8-36CKM available from ECS Inc.; however, it should be appreciated that any crystal oscillator that can communicate with microcontroller 160 and keep time can be utilized. Antenna 164 is operatively arranged to communicate with microcontroller 160 and can be utilized to send/receive a wireless signal/communication. It should be appreciated that "wireless communication(s)" as used herein is intended to mean Radio Frequency Identification (RFID) communication, Bluetooth® protocols, Near field Communication (NFC), Near Field Magnetic Inductance Communication (NFMIC), Wi-Fi, LTE, Airdrop® communication, or any other wireless protocol sufficient to communicate with microcontroller 160. Additionally, display 136 is capable of rendering a visible image, e.g., a bar code or QR code, which can be scanned by an external device as a means for transmitting information from dispensing assembly 100. In some embodiments, antenna 164 is part no.: 2450AT42E0100 available from Johanson Technology Inc.; however it should be appreciated that any antenna capable of communication via the above-identified protocols can be used. Power supply 166 is intended to be a battery or any combination of multiple batteries that can produce sufficient voltage to power the components in first circuit 138, solenoid actuator 152, and display 136. Flex circuit 168 is a flexible ribbon-type circuit that is operatively arranged to bend and flex such that electrical current may still flow from microcontroller 160 to display 136. Furthermore, sensor 169 is arranged to sense and store the rotational position of tablet disc 122. It should be appreciated that a sensor 169 could be embodied as an optical sensor, limit-switch, or other device capable of sensing a position of tablet disc 122 can be included in first circuit 138.

Figure 4B:
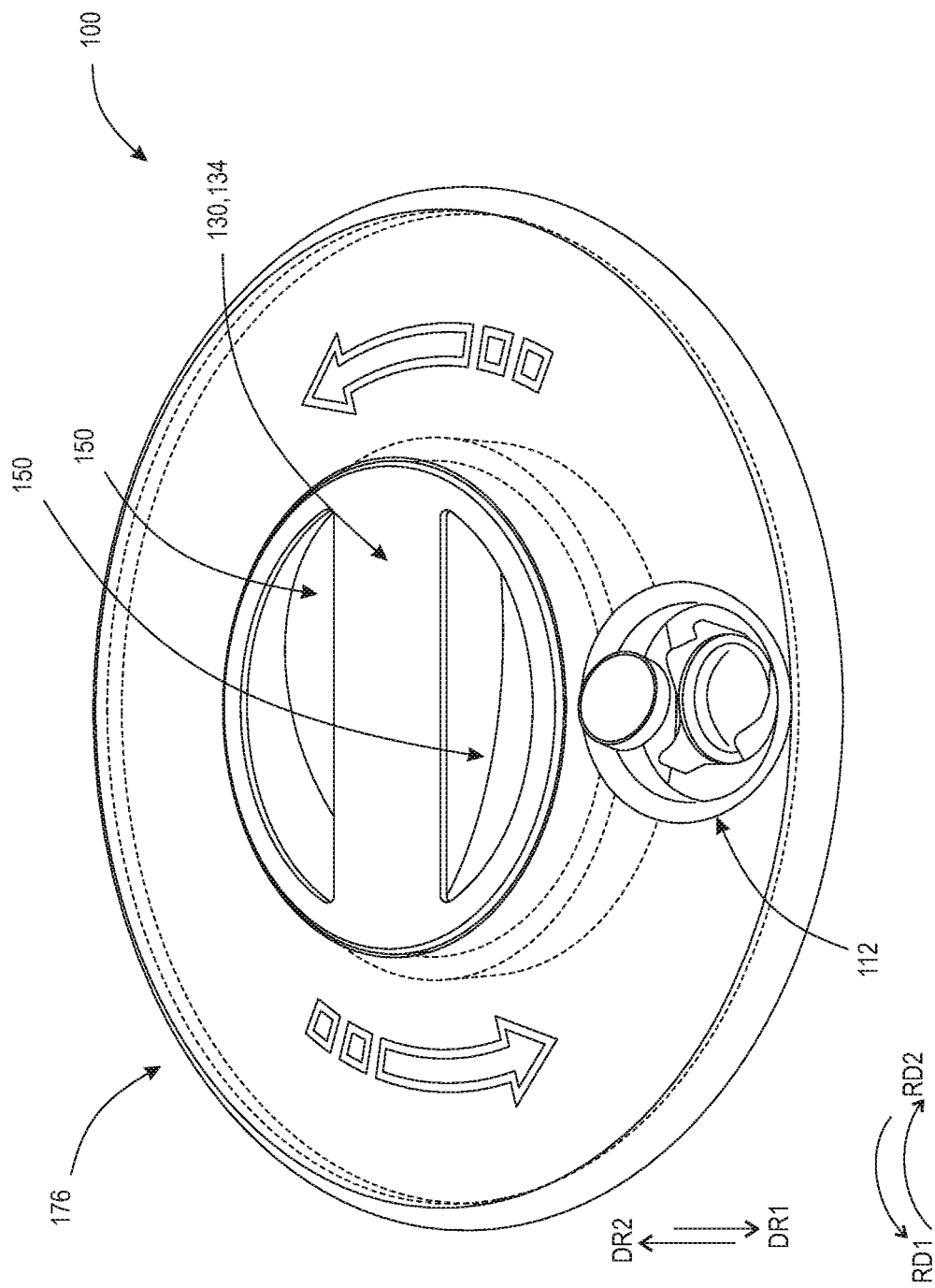
FIG. 4B is a front perspective view of the bottom of the dispensing assembly.

The following description is intended to illustrate one potential operation of dispensing assembly 100 and should be read in view of FIGS. 4A-5C. Initially, a user will receive dispensing assembly 100 from the manufacturer, pharmacist, or other healthcare professional. The dispensing assembly will come pre-assembled and closed as illustrated in FIGS. 4A and 4B. In initial position 176, one tablet of plurality of tablets 124 is aligned with first aperture 110 and second aperture 112 and can be depressed and removed from tablet disc 122 by the user. Additionally, in initial position 176, display 136 indicates that the first tablet, aligned with apertures 110 and 112, is available for dispensing. Once the first tablet of plurality of tablets 124 is dispensed, the user can ingest the tablet. In initial position 176, ratchet 158 (shown in FIGS. 2A and 2B), which is pivotably mounted on second rim 120 (shown in FIG. 2A) of inferior component 106, is spring loaded such that it is engaged with one of the second plurality of teeth 156 (shown in FIG. 2A) of second component 134 preventing rotation of lock 130 in second rotational direction RD2. Second plurality of teeth 156 and ratchet 158 are arranged such that they are not affected by vibrations or gyrations which could be experience in the average use of the assembly. Additionally, in initial position 176 solenoid actuator 152 (shown in FIGS. 2A and 2B) is in an activated state, i.e., positioned such that the plunger is in an extended position. In this extended position, solenoid actuator 152 engages with pivotable catch 154 (shown in FIGS. 2A and 2B). Pivotable catch 154 pivots about a peg or other protrusion which is disposed within a third cavity on first surface 142 (shown in FIG. 2A) of first projection 140 (shown in FIG. 2A) of second component 134. In this state, pivotable catch 154 is not engaged with first plurality of teeth 116 (shown in FIG. 2B) of superior component 104, and second component 134 and tablet disc 122 are free to rotate in second rotational direction RD2.

Figure 5A:
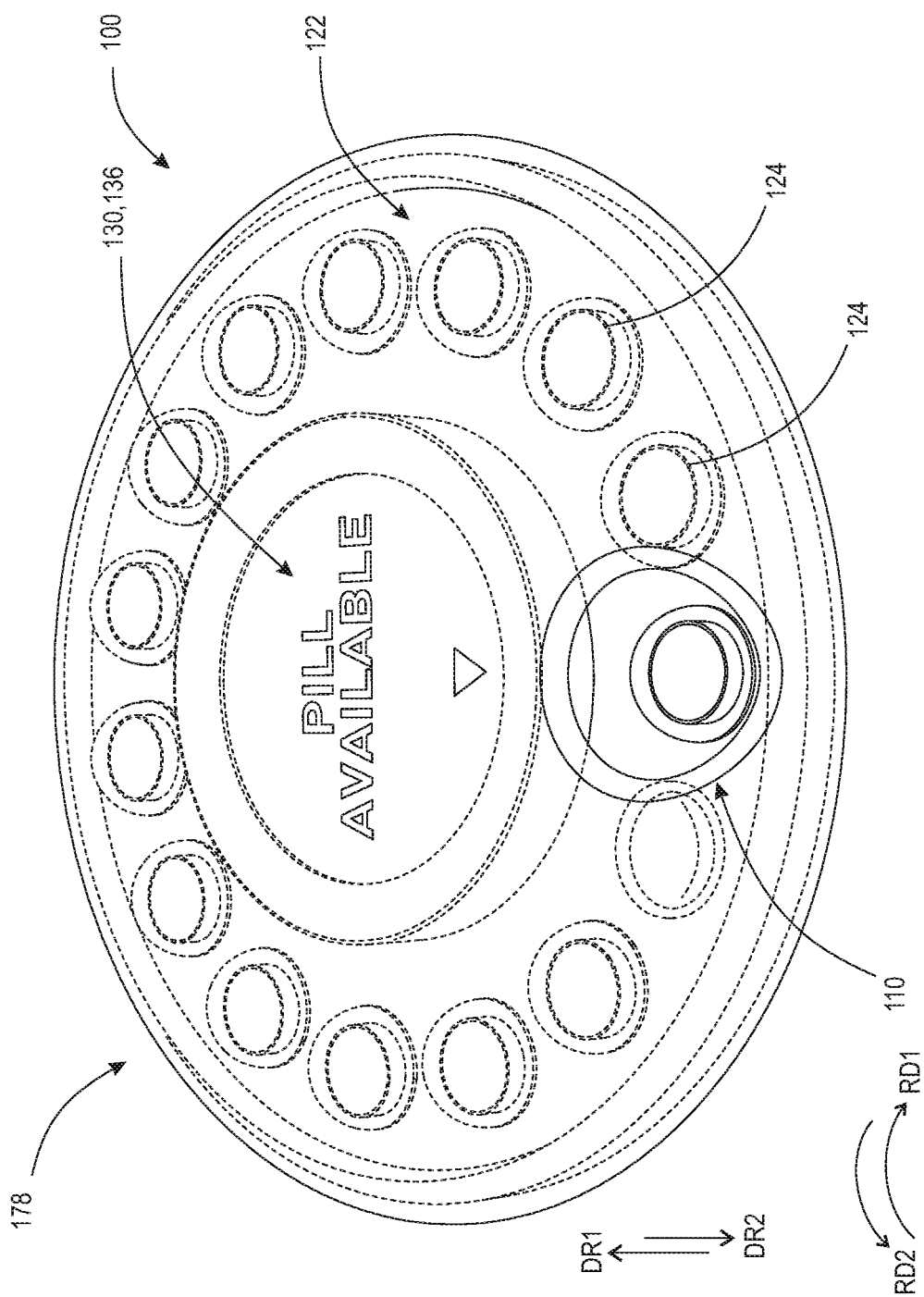
FIG. 5A is a front perspective view of the top of the dispensing assembly.
Figure 5B:
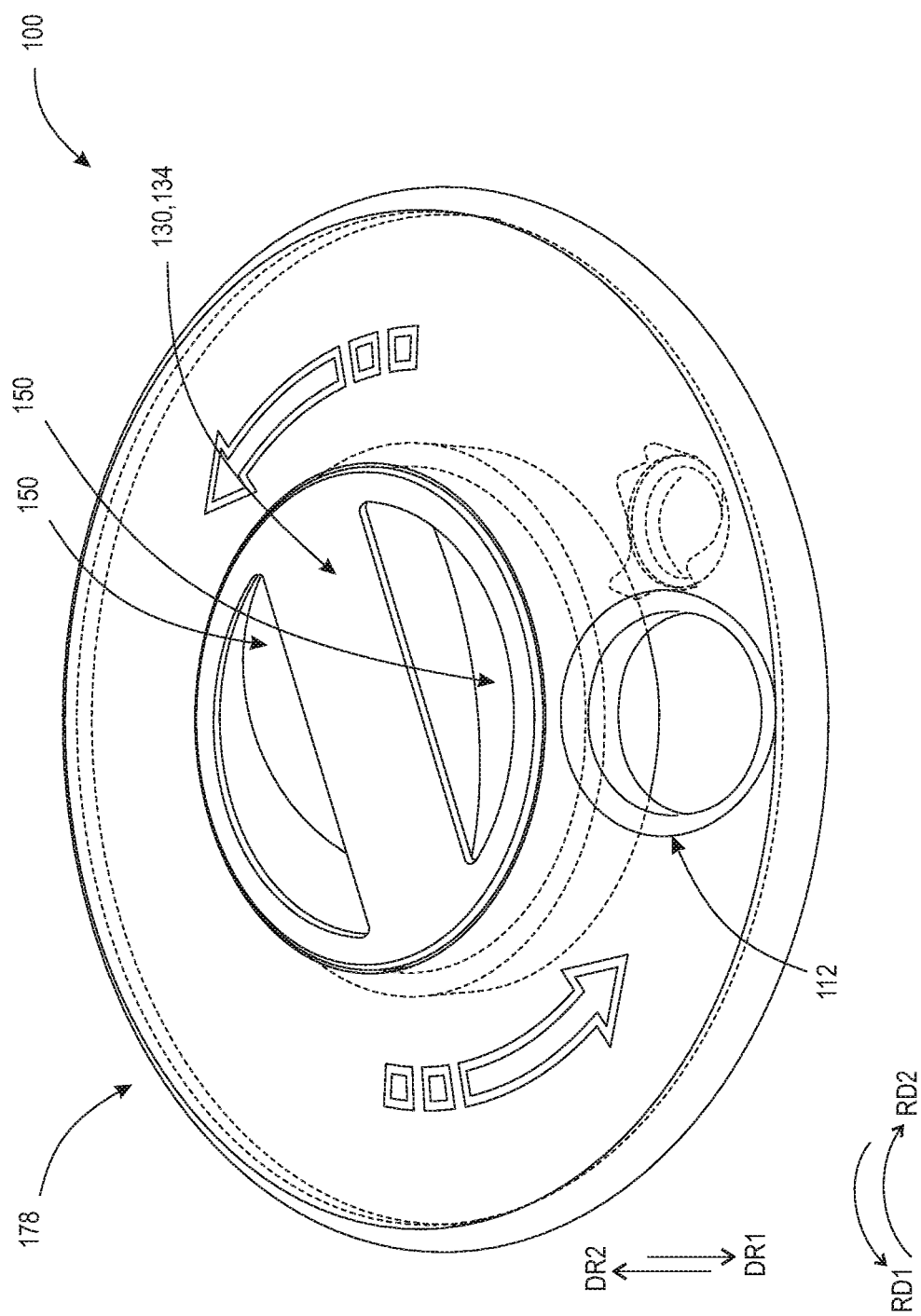
FIG. 5B is a front perspective view of the top of the dispensing assembly.
Figure 5C:
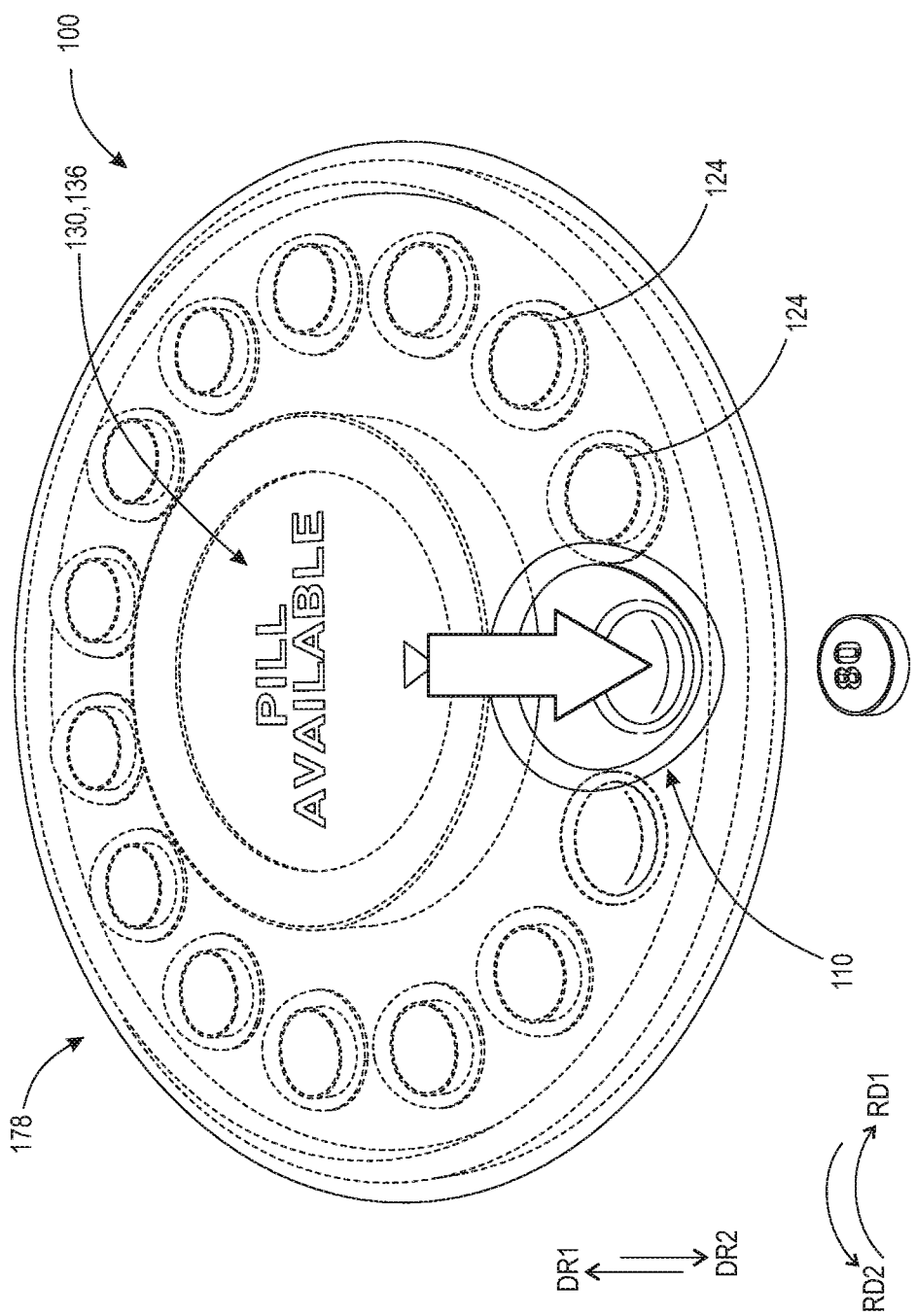
FIG. 5C is a front perspective view of the top of the dispensing assembly.

To advance the dispensing assembly to second position 178, illustrated in FIGS. 5A-5C, the user engages with plurality of grips 150 disposed on second surface 148 of the second component 134 of lock 130. The user applies a rotational force in first rotational direction RD1. When sensor 169 indicates that tablet disc 122 has been rotated to second position 178. Activation of sensor 169 simultaneously causes solenoid actuator 152 to retract and timer 162 to activate, beginning a counting down proportional to first time interval 188 discussed infra. When solenoid actuator 152 is in the retracted state, pivotable catch 154 will engage with one of first plurality of teeth 116 of superior component 104 and prevent further rotational motion in second rotational direction RD2. Although not illustrated this may be accomplished with some biasing device, e.g., a spring, which biases pivotable catch 154 towards first plurality of teeth 116. Once in second position 178, a second tablet will be positioned and aligned with apertures 110 and 112 allowing the second tablet to be dispensed from dispensing assembly 100. At this point, the user must wait until the expiration of first time interval 188, for solenoid actuator 152 to engage with pivotable catch 154 and allow for rotation of tablet disc 122 to the next position. This process is repeated until all of the tablets of plurality of tablets 124 are utilized. Once the tablet disc is empty, the user can either dispose of the device, or return it to their healthcare provider for further analysis of usage discussed infra.

It should also be appreciated that the first pill/tablet slot of tablet disc 122 can be left empty, i.e., without a tablet present. This arrangement would be utilized in situations where a patient has been given a first dose of medication via a healthcare provider. In this situation, the healthcare provider or user would then rotate tablet disc 122 into second position 178 and trigger the countdown proportional to first time interval 188.

Figure 6A:
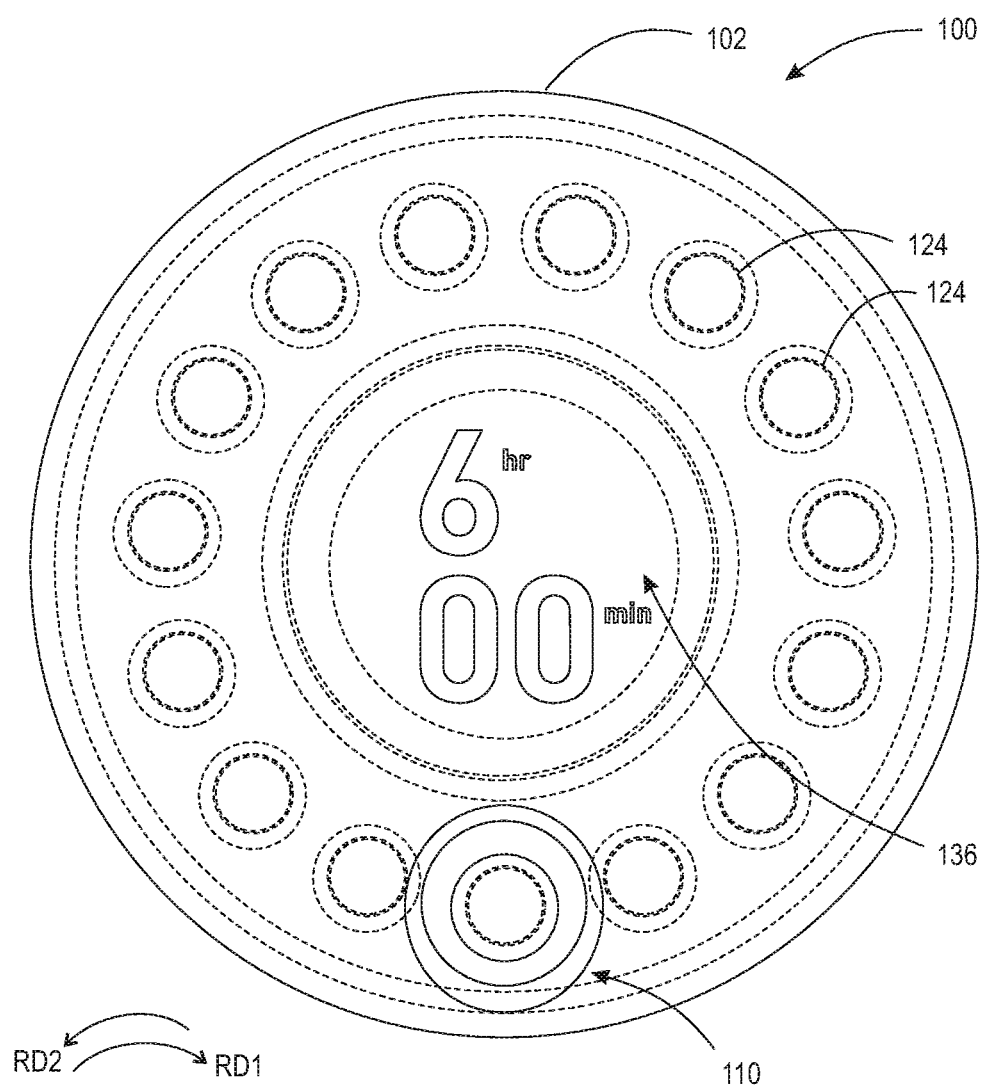
FIG. 6A is a top plan view of a dispensing assembly.
Figure 6B:
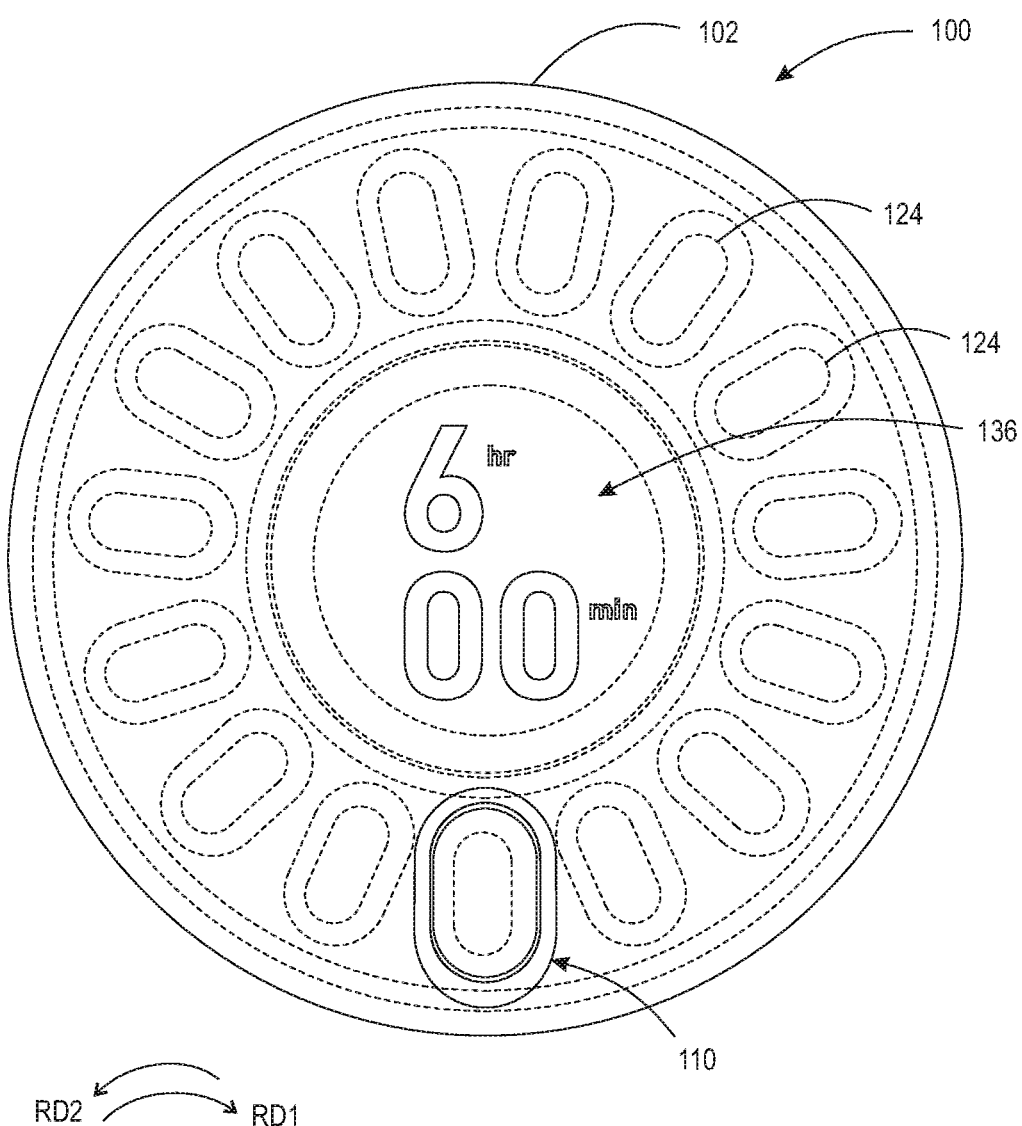
FIG. 6B is a top plan view of a dispensing assembly.

FIGS. 6A and 6B illustrate a top plan view of dispensing assembly 100. These views illustrate some of the potential variations in size and shape of tablets which can be utilized in tablet disc 122. The tablets of plurality of tablets 124 can be shaped as ovoid, cylindrical, triangular, or other suitable shape for ingestion. It should be appreciated that the variations shown are non-exhaustive of the potential sizes and shapes available. For example, any shape tablet can be used that can be pushed through apertures 110 and 112.

Figure 7:
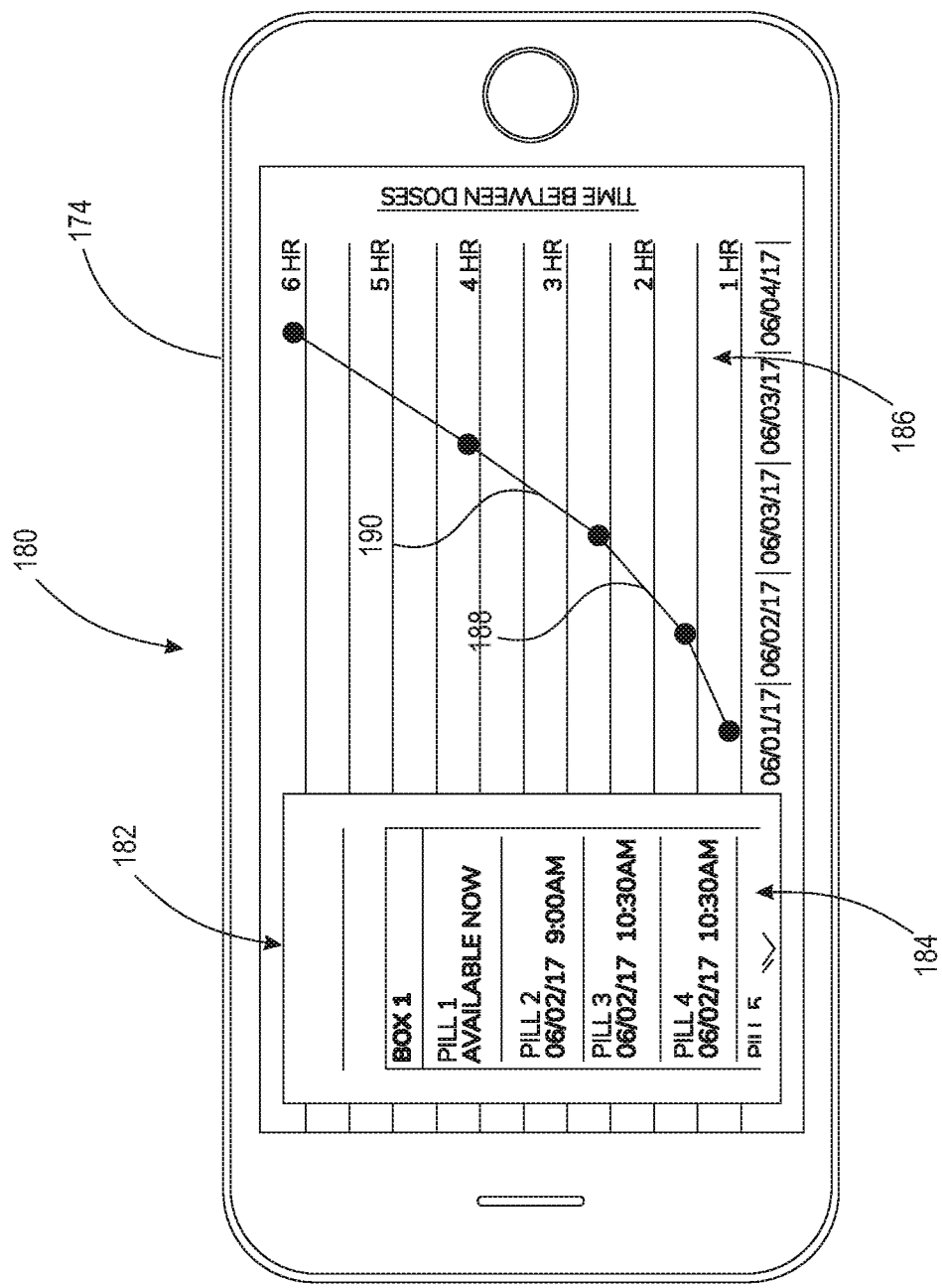
FIG. 7 is a schematic view of a software interface arranged for communication with the dispensing assembly.

FIG. 7 illustrates a schematic view of first computer 174 and software interface 180. First computer 174 and software interface 180 are arranged for communication with dispensing assembly 100. Software interface 180 is arranged to display first medication 182, list 184 arranged to show an organized list of the various dates and times each pill/tablet will become available, and graph 186 arranged to show a graphical illustration of the various dates and times recorded in list 184. In some embodiments, first computer 174 is a smart phone; however, it should be appreciated that any other computer capable of sending and receiving wireless communications with antenna 164 can be used. First computer 174 is operatively arranged to receive/transmit wireless communications to and from antenna 164 discussed supra. First computer 174 may send an initial query to antenna 164, which query can be electrically transferred to microcontroller 160. Although not illustrated, it should also be appreciated that dispensing assembly 100 can communicate with first computer 174 via a wired connection, e.g., Ethernet cable, USB cable, or docking station. Microcontroller 160 can retrieve the data of the first data set, discuss supra, from memory 172 and transmit the first data set from antenna 164 to first computer 174 for display in software interface 180 of first computer 174. It should be appreciated that software interface 180 can be arranged to display more than one medication, e.g., a second medication, third medication, fourth medication simultaneously.

It should also be appreciated that multiple time intervals can be set by the pharmacist, manufacturer, or other healthcare provider, e.g., first time interval 188 and second time interval 190. First time interval 188 and second time interval 190 can be identical or they can be different e.g., the time between access to the first tablet and second tablet can be different than the time interval between the third tablet and fourth tablet. Additionally, the time intervals can vary e.g., the time between access to each tablet can range from days to seconds. It should further be appreciated that a final time period may be utilized in addition to first time interval 188 and second time interval 190. The final time period can be utilized to set a value of time that, when expired, renders the device rotationally locked until accessed by the pharmacist, manufacturer, or other healthcare provider. For example, a final time period could be utilized in the event the dispensing assembly is used to administer doses of medication for clinical trials. If a clinical trial, having a set period of 10 days is established, the device may allow access to each tablet at predetermined time intervals in addition to locking the device permanently at the end of the ten day period. This would allow the administrators of the trial to gather evidence of a patient failing to take the medications at the prescribed time intervals.

FIG. 8 is top plan view of dispensing assembly 100 in an assembled state. In this view, the interaction between ratchet 158 and second plurality of teeth 156, as well as the interaction between pivotable catch 154 and first plurality of teeth 116 can be seen. This view also illustrates the interaction between solenoid actuator 152 and pivotable catch 154, in that, the actuator plunger of solenoid actuator 152 sits within a notch arranged within pivotable catch 154.

Figure 9A:
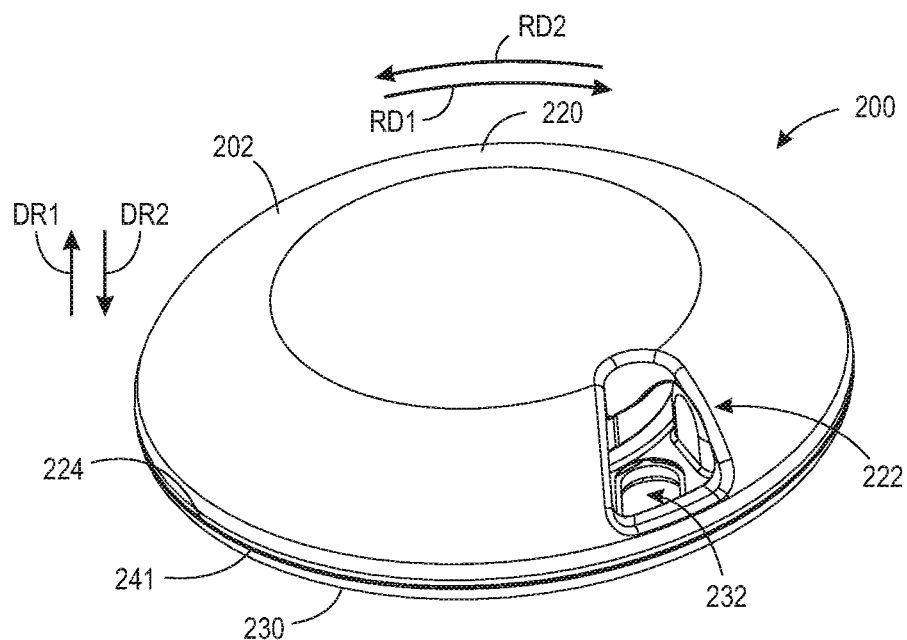
FIG. 9A is a front top perspective view of a dispensing assembly.
Figure 9B:
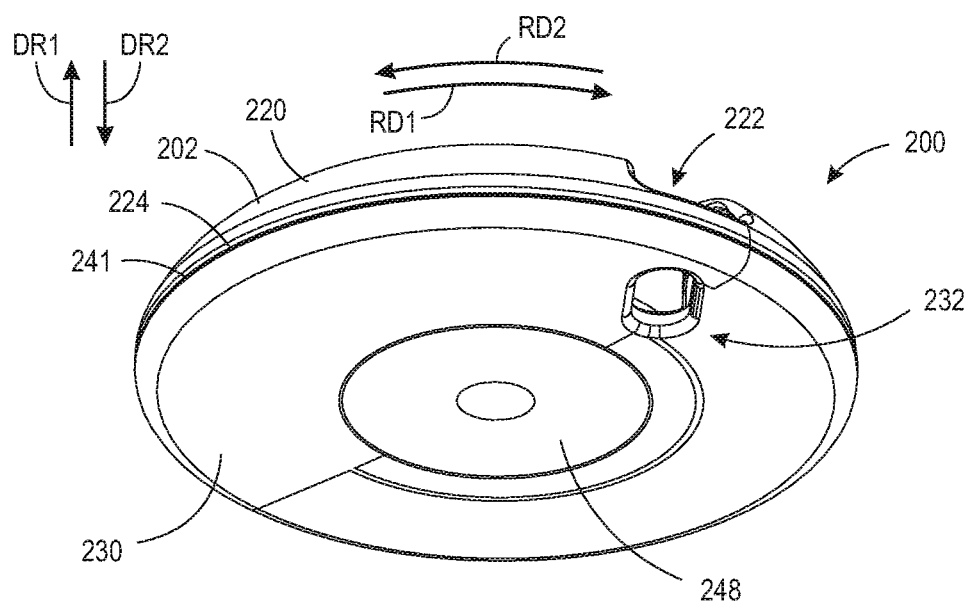
FIG. 9B is a front bottom perspective view of the dispensing assembly shown in FIG. 9A.
Figure 10:
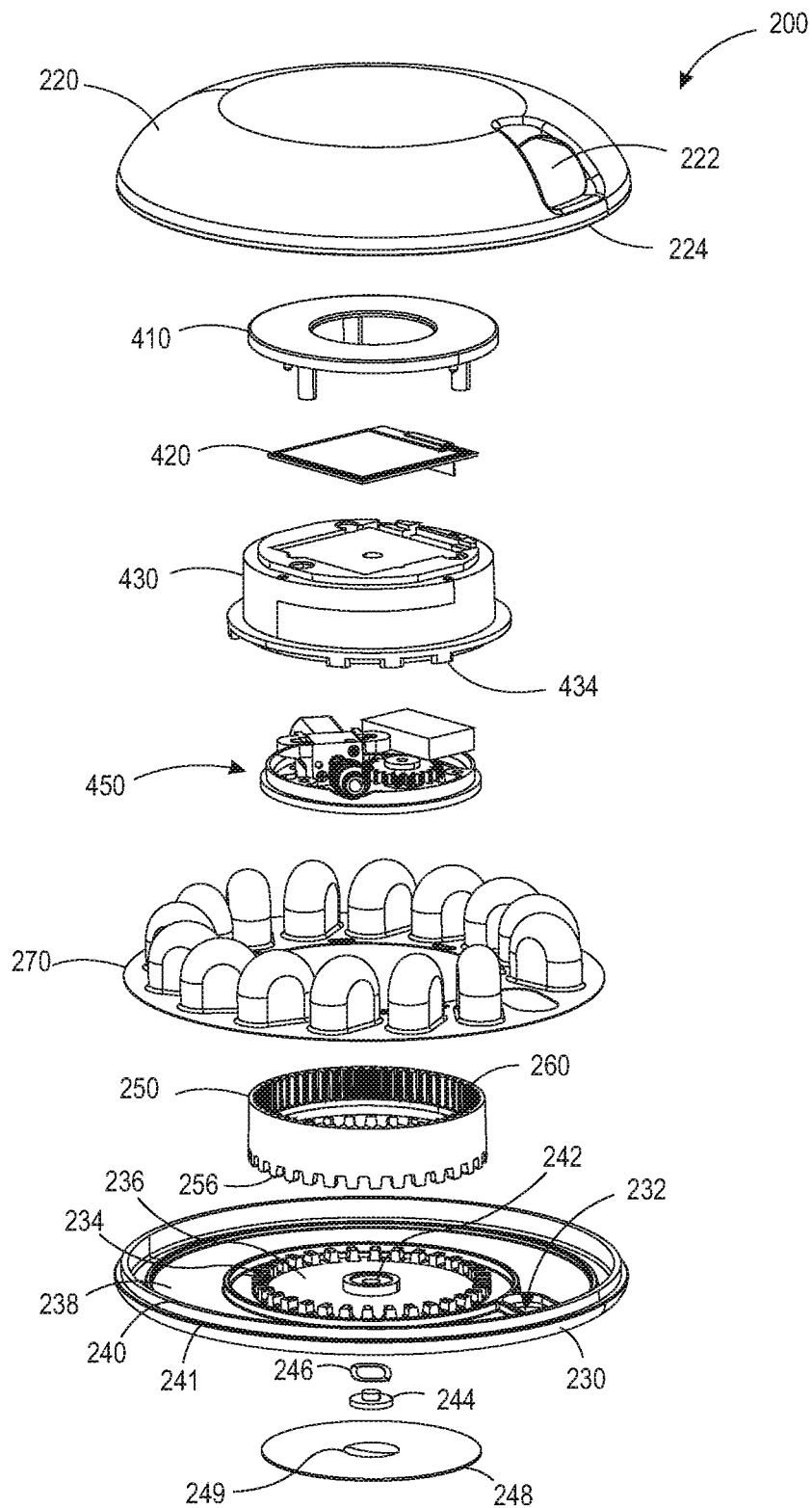
FIG. 10 is a front perspective exploded view of the dispensing assembly shown in FIG. 9A.

FIG. 9A is a front top perspective view of dispensing assembly 200. FIG. 9B is a front bottom perspective view of dispensing assembly 200. FIG. 10 is a front perspective exploded view of dispensing assembly 200. Dispensing assembly 200 generally comprises assembly 204 and assembly 206.

Figure 11A:
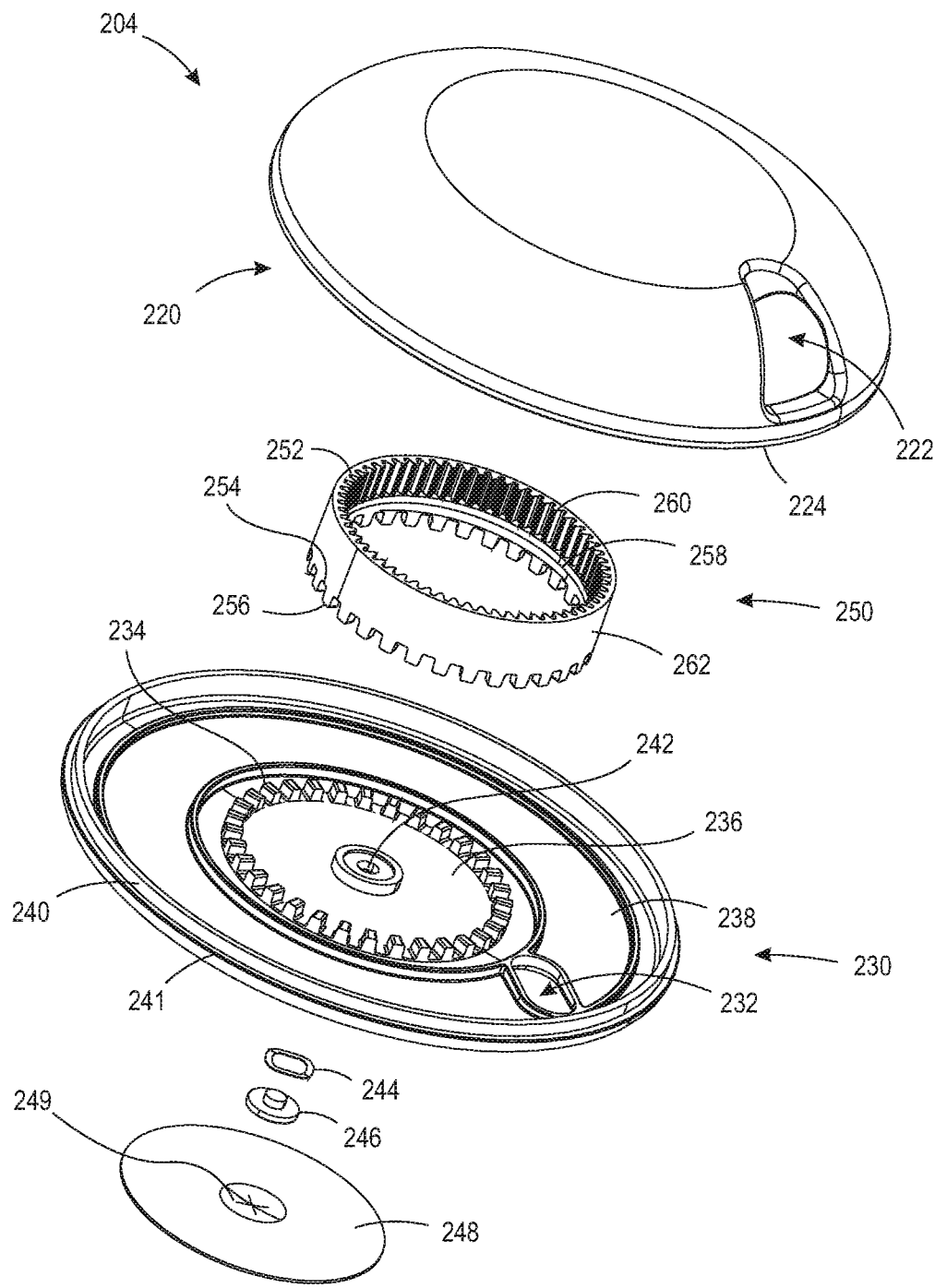
FIG. 11A is a top perspective exploded view of an assembly of the dispensing assembly shown in FIG. 9A.
Figure 11B:
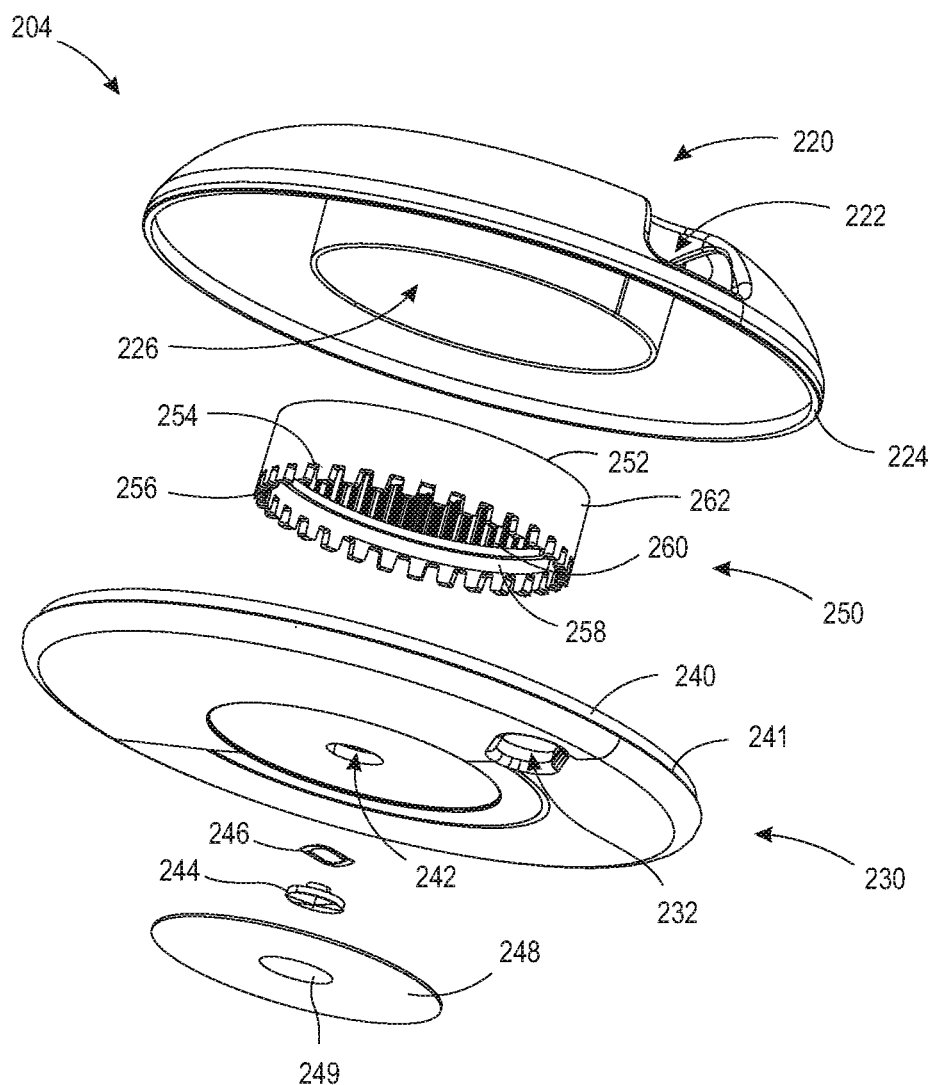
FIG. 11B is a bottom perspective exploded view of the assembly shown in FIG. 11A.

FIG. 11A is a top perspective exploded view of assembly 204 of dispensing assembly 200. FIG. 11B is a bottom perspective exploded view of assembly 204. The following descriptions should be read in view of FIGS. 9A-11B. Assembly 204 generally comprises case 202 and drive gear 250. Case 202 comprises superior component 220, inferior component 230, and cover 248. Case 202 is substantially toroidal in shape and the connection of superior component 220 to inferior component 230 leaves a substantially toroidal cavity therebetween.

Superior component 220 comprises aperture 222, bottom edge 224, and hole 226. Hole 226 is arranged to fit around drive gear 250 and electronics assembly 400, as will be discussed in greater detail below. Inferior component 230 comprises aperture 232, teeth 234, surface 236, surface 238, flange 240 having edge 241, and hole 242. Inferior component 230 is arranged to be non-rotatably connected to superior component 220 and drive gear 250. Specifically, superior component 220 is arranged to non-rotatably connect to flange 240 such that bottom edge 224 abuts against or is arranged substantially proximate to edge 241. Superior component 220 may be connected to inferior component 230 via a press or interference fit. It should be appreciated, however, that any suitable means for non-rotatably connecting superior component 220 to inferior component 230 may be used, such as adhesives, bolts, screws, rivets, nails, welding, etc. In some embodiments, superior component 220 is connected to inferior component 230 such that the only way to disconnect the two components is to destroy case 202. In some embodiments, superior component 220 is connected to inferior component 230, and they are arranged such that once they are fitted together, no user can open the case, e.g., only a manufacturer or healthcare professional may separate the components. In some embodiments, superior component 220 and inferior component 230 are made of high impact modified Poly(methyl methacrylate) (PMMA); however, it should be appreciated that any other durable material can be used, e.g., high-density polyethylene, low-density polyethylene, metal, high-impact polystyrene, Polycarbonate (PC), Polyether Imide (PEI), or any other material which can resist breaking or cracking while in use, and prevent tampering and/or render evident any tampering caused by the user. Apertures 222 and 232 are arranged such that when case 202 is assembled, aperture 222 of superior component 220 is aligned with, and directly above, aperture 232 of inferior component 230. As shown, teeth 234 extend from surface 236 and are arranged to engage with teeth 256 of drive gear 250, as will be discussed in greater detail below. Superior component 220 and inferior component 230 are preferably translucent or transparent such that the user can see how many pills or tablets are left therein. In some embodiments, superior component 220 and inferior component 230 are opaque. In some embodiments, only one of the superior component 220 and inferior component 230 is opaque.

Drive gear 250 comprises top surface 252, bottom surface 254 having a plurality of teeth 256, radially inward facing surface 258 having a plurality of teeth 260, and radially outward facing surface 262. Drive gear 250 is arranged to engage inferior component 230. Specifically, teeth 256 engage teeth 234 to non-rotatably connect drive gear 250 to inferior component 230. Teeth 260 are operatively arranged to engage idler gear 472 of motor assembly 450 such that motor 460 rotates electronics assembly 400 relative to drive gear 250 and case 202 (i.e., superior component 220 and inferior component 230), as will be discussed in greater detail below.

Assembly 204 may further comprise plunger 244, spring 246, and/or cover 248. Spring 246 may be arranged in hole 242 or in a counter-bore of hole 242 axially between inferior component 230 and plunger 244. Spring 246 holds plunger 244 above switch 496. Plunger 244 engages hole 242 via a slip or clearance fit. Plunger 244 is operatively arranged to, when displaced by a user, engage switch 496, as will be discussed in greater detail below. In some embodiments, plunger 244 comprises acrylonitrile butadiene styrene (ABS). Cover 248 is generally plate-shaped and may comprise a spherical curvature. Cover 248 is non-rotatably connected to inferior component 230 via any suitable means, such as adhesives, glue, rivets, screws, bolts, nails, welding, etc. Cover 248 comprises portion 249. Portion 249 is elastomeric and may be rounded such that it can be pressed/displaced to engage plunger 244 and/or switch 496 and return to its original shape. In some embodiments, dispensing assembly 200 does not require spring 246 or plunger 244. In such embodiments, portion 249 is displaced and directly engages switch 496. In some embodiments, cover 240 comprises plastic or vinyl.

Figure 12A:
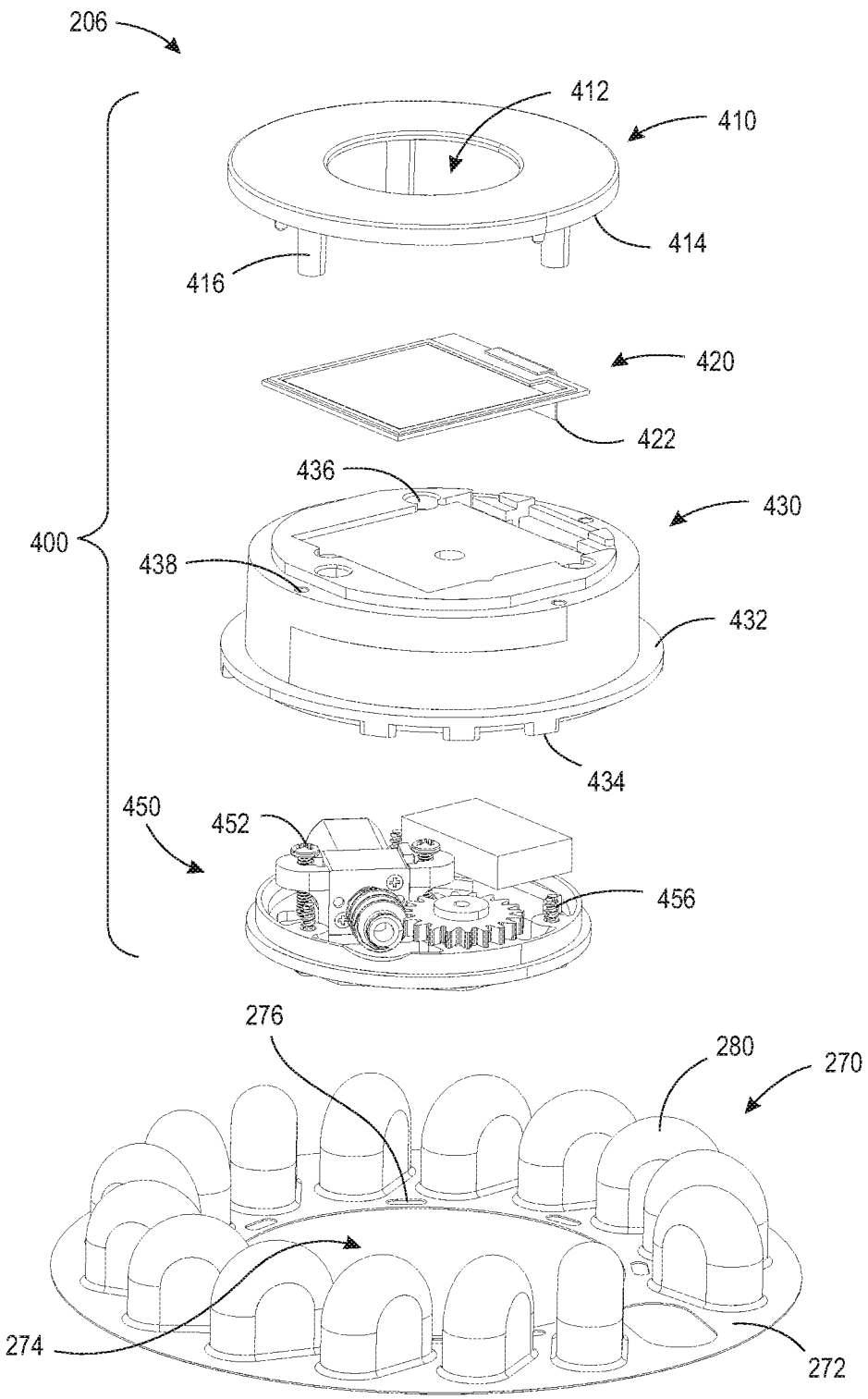
FIG. 12A is a top perspective exploded view of an assembly of the dispensing assembly shown in FIG. 9A.
Figure 12B:
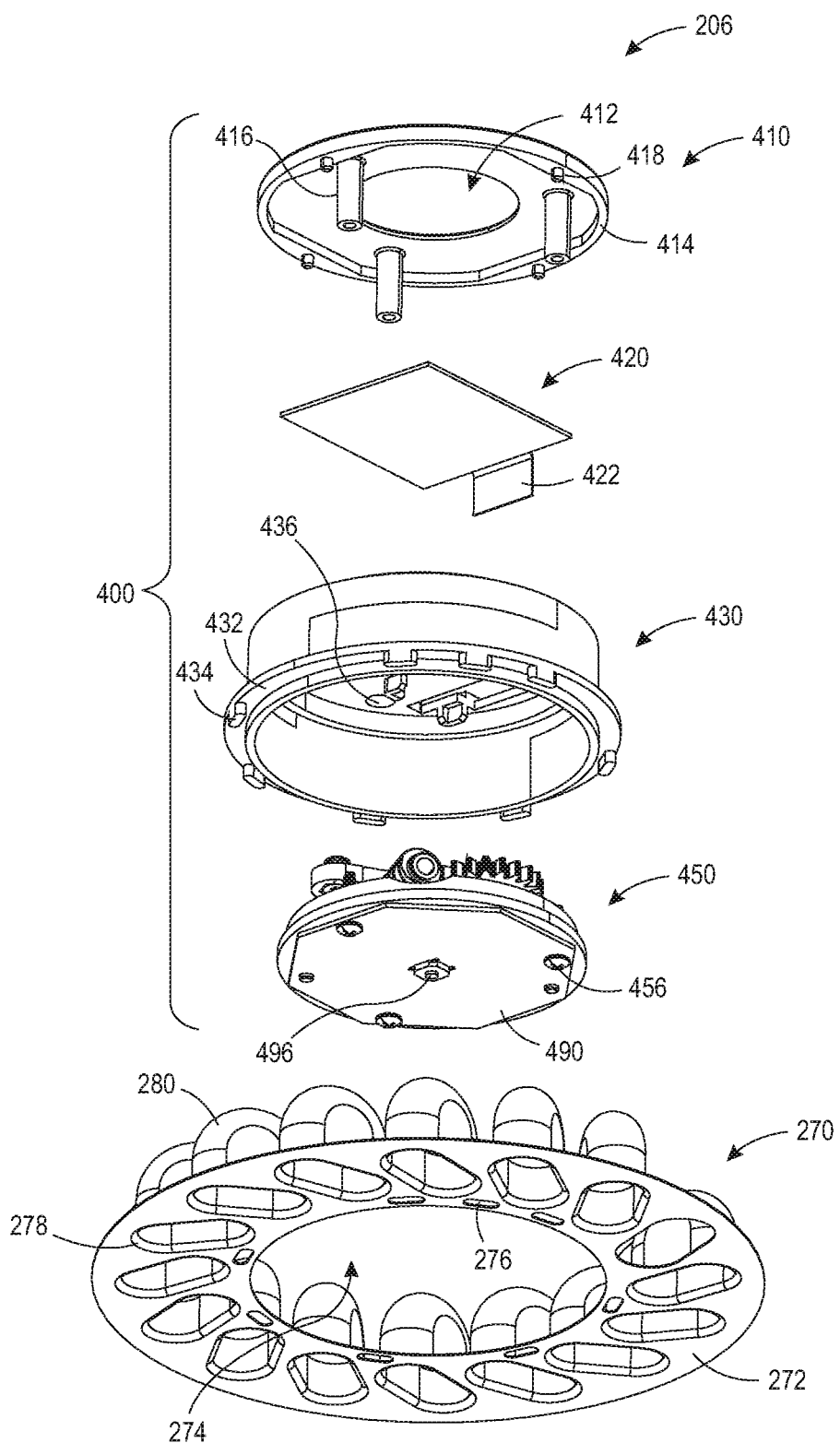
FIG. 12B is a bottom perspective exploded view of the assembly shown in FIG. 12B.

FIG. 12A is a top perspective exploded view of assembly 206 of dispensing assembly 200. FIG. 12B is a bottom perspective exploded view of assembly 206. The following description should be read in view of FIGS. 9A-10 and 12A-B. Assembly 206 generally comprises blister pack or tablet disc 270 and electronics assembly 400.

Blister pack 270 is arranged in case 202 and comprises disc 272, through-bore or hole 274, apertures 276, apertures 278, and compartments 280. Blister pack 270 is rotatably arranged on inferior component 230. Specifically, disc 272 is arranged on surface 238. Compartments 280 are arranged to hold one or more tablets or pills (not shown). As blister pack 270 is rotated relative to case 202, respective compartments 280 align with apertures 222 and 232 such that the user can push the respectively aligned compartment 280 through aperture 222, and the pill or tablet is displaced out of compartment 280 through aperture 278 and aperture 232. In some embodiments, a thin film or foil may cover apertures 278 to seal the pills or tablets within compartments 280. In some embodiments, compartments 280 are set apart from each other a fixed circumferential distance such that they are evenly spaced. In some embodiments, compartments 280 are set apart from each other a fixed circumferential distance such that they are not evenly spaced. In some embodiments, blister pack 270 is a prefabricated blister pack with a plurality of compartments 280 which isolate a single dose of a particular medication, i.e., each tablet is intended to be a single dose of a particular medication. The distance between each tablet or compartment and the size of apertures 222 and 232 are proportional such that access to tablets is limited to one tablet at a time through apertures 222 and 232. One or more apertures 276 are arranged for engagement with one or more protrusions 434 of housing 430 to non-rotatably connect blister pack 270 and electronics assembly 400, as will be discussed in greater detail below.

Electronics assembly 400 comprises bezel 410, display 420, housing 430, and motor assembly 450. It should be appreciated that when electronics assembly 400 is fully assembled, bezel 410, display 420, housing 430, and motor assembly 450 are all non-rotatably connected to each other. In some embodiments, when electronics assembly 400 is fully assembled, bezel 410, display 420, housing 430, and motor assembly 450 are all fixedly secured to each other. Bezel 410 comprises hole 412, surface 414, and nuts 416. Bezel 410 is generally a bracket arranged to be fixedly secured to motor assembly 450 via retainer screws 456 and nuts 416, thereby securing display 420 and housing 430 to motor assembly 450. Nuts 416 project from surface 414, extend through apertures 436, and are threadably engaged with retainer screws 456, as shown. In some embodiments, when bezel 410 is fully connected to motor assembly 450, display 420 and/or housing 430 is axially clamped between surface 414 and motor assembly 450. In some embodiments, bezel 410 further comprises dowels 418 protruding from surface 414. Dowels 418 engage holes 438 to non-rotatably connect bezel 410 and housing 430. Hole 412 allows the user to view display 420 therethrough. Hole 412 is shown as being circular in the figures; however, it should be appreciated that hole 412 may be any geometric shape suitable to view display 420, such as triangular, ovular, ellipsoidal, rectangular, square, trapezoidal, etc.

Display 420 is non-rotatably connected to housing 430 via any suitable means, for example, adhesives, rivets, screws, bolts, nails, welding, soldering, etc. Display 420 is electrically connected to circuit board 490 via cable 422. Cable 422 extends from display 420, through housing 430, and connects to plug 494 of circuit board 490. In some embodiments, cable 422 is a ribbon cable. In some embodiments, display 420 is an E-ink display; however, it should be appreciated that other displays are possible, e.g., a touch-screen display, a Light-Emitting Diode (LED) display, an Electroluminescent (EL) display, a Plasma Display Panel (PDP) display, an Organic Light-Emitting Diode (OLED) display, a Liquid Crystal (LCD) display, or other equivalent displays. One advantage of using an E-ink or electronic paper display is that the time that the next pill will be available will continue to be displayed even though display 420 has been shut down, to avoid unnecessarily draining the batter/power source. Display 420 is arranged to display the current state of dispensing assembly 200 and show the time interval remaining until blister pack 270 can be rotated to the next position. It should be appreciated that display 420 can be used to display any information deemed important for the prescription of the medication; for example: a prompt to PRESS BUTTON (portion 249) TO START; a prompt TO START PLACE TAG NEAR DEVICE indicating that the user should place the wireless tag near device (as will be discussed in greater detail below); the time that the next pill will be available; the time remaining until the next pill is available; a prompt that NEXT PILL IS READY indicating that the user can press the button (portion 249) to signal dispensing assembly 200 to rotate the pills; a prompt that NEXT PILL IS READY indicating that the user can place the wireless tag near the device to signal dispensing assembly 200 to rotate the pills; a prompt that RX (prescription) IS COMPLETE and/or RETURN TO PHARMACY; a Quick Response (QR) code indicating information about the device, patient, medication, etc.; medication information; prescription information; medication warning information; and, a failure state indicating that dispensing assembly has failed or the prescription has been stopped, which may include a prompt RX STOPPED PLEASE VISIT DOCTOR.

Housing 430 is generally cylindrical and is arranged to encase and protect motor assembly 450 as well as drive gear 250. Housing 430 comprises flange 432 having one or more downward extending protrusions 434. Protrusions 434 are arranged to engage apertures 276 of blister pack 270 to non-rotatably connect housing 430 and blister pack 270. Housing 430 further comprises apertures 436, through which nuts 416 extend to connect to retainer screws 456. Apertures 436 may be any geometry suitable for engagement with nuts 416, such as triangular, square, rectangular, circular, ovular, etc. Housing 430 may further comprise holes 438 arranged to engage dowels 418, as previously discussed.

Figure 13:
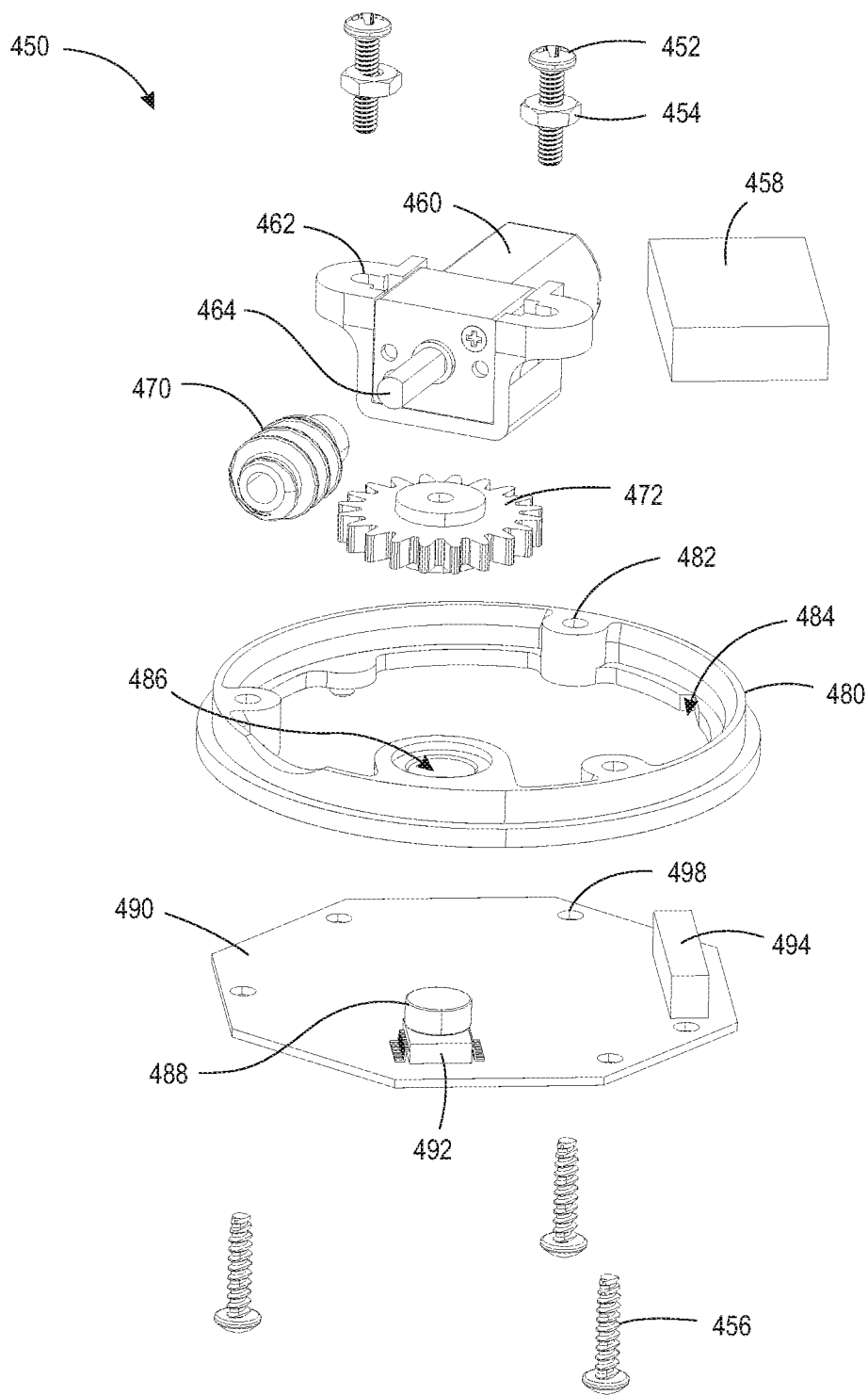
FIG. 13 is a perspective exploded view of a motor assembly as shown in FIGS. 10-12B.

FIG. 13 is a perspective exploded view of motor assembly 450. Motor assembly 450 comprises power supply 458, motor 460, worm drive 470, idler gear 472, retainer 480, and circuit board 490. Power supply 458 is intended to be a battery or any combination of multiple batteries that can produce sufficient voltage to power the components of dispensing assembly 200, including motor 460, display 420, encoder 492, circuit board 490, and any other component of dispensing assembly 200 that may require power. Motor 460 is generally an electric motor comprising shaft 464. Motor 460 is mounted to housing 430 via motor mounting screws 452 and motor mounting nuts 454. Worm drive 470 is non-rotatably connected to shaft 464. Motor 460 is arranged to rotate worm drive 470, which is engaged with idler gear 472 to rotate drive gear 250, as will be discussed in greater detail below. Retainer 480 comprises holes 482, slot 484, and hole 486. Idler gear 472 is rotatably connected to retainer 480 via hole 486. A portion of idler gear 472 engages hole 486, and idler gear 472 rotates therein. Circuit board 490 is secured to retainer 480 via retainer screws 456. Specifically, retainer screws 456 extend up through holes 498 and 482, and secure into nuts 416. Circuit board 490 comprises encoder 492, encoder magnet 488, plug 494, and switch 496. When motor assembly 450 is assembled, encoder magnet 488 and encoder 492 are aligned with and positioned under idler gear 472, and plug 494 fits within slot 484.

Encoder 492 is a magnetic encoder which works in conjunction with encoder magnet 488 and idler gear 472 to sense the rotation of idler gear 472. In some embodiments, idler gear 472 comprises a ferrous metal. Idler gear 472 comprises precisely machined teeth that provide a code pattern. As idler gear 472 rotates, these teeth disturb the magnetic flux emitted by encoder magnet 488, causing the flux field to expand and collapse. These changes in the magnetic field are sensed by encoder 492, which generates a corresponding digital or pulse signal output. For example, once idler gear 472 has rotated a predetermined amount (i.e., idler gear 472 has rotated to align the next tablet for removal from dispensing assembly 200), encoder 492 sends a signal to circuit board 490 to stop motor 460. Encoder 492 and encoder magnet 488 may act as a Hall effect device, which senses a change in voltage, or a magnetoresistive device, which senses a change in magnetic field. In some embodiments, encoder 492 and encoder magnet 488 may be replaced by a sensor (e.g., optical sensor) operatively arranged to sense and store the rotational position of idler gear 472, drive gear 250, and/or blister pack 270. It should be appreciated that electronics assembly 400 may be programed to rotate to align any of the plurality of compartments 280 with apertures 222 and 232, not just the "next compartment." For example, each compartment of plurality of compartments 280 is given a label (e.g., compartments A-O), with various medications being arranged therein, and depending on which medication needs to be taken at that time, motor rotates blister pack 270 to align the desired compartment with apertures 222 and 232.

Circuit board 490 may further comprise the same or substantially similar components to that of first circuit 138 as described in reference to FIG. 3. As such, circuit board 490 may further comprise microcontroller 160, timer 162, antenna 164, and sensor 169 (in addition to or in place of encoder 492 and encoder magnet 488 as previously discussed). Microcontroller 160 further includes processor 170 and memory 172, which are operatively arranged to store and execute a set of non-transitory computer readable instructions. Memory 172 can store a first data set comprised of at least one date, at least one time, a rotational position of the tablet disc, and an integer. The date, time, and integer can reflect the history of a user's interaction with dispensing assembly 200 and keep track of which pill/tablet was accessed at what time. In some embodiments, microcontroller 160 is a Cypress Semiconductor part no.: CY8C4247LQI-BL483 available from Mouser Electronics; however, it should be appreciated that any other suitable microcontroller could be used to store the set of non-transitory computer readable instructions and first data set.

Timer 162 is a simple circuit operatively arranged to provide a base time signal to a microcontroller. This circuit comprises, for example, a crystal quartz oscillator. In some embodiments, timer 162 is a crystal oscillator part no.: ECS-240-8-36CKM available from ECS Inc.; however, it should be appreciated that any crystal oscillator that can communicate with microcontroller 160 and keep time can be utilized. Antenna 164 is operatively arranged to communicate with microcontroller 160 and can be utilized to send/receive a wireless signal/communication. It should be appreciated that "wireless communication(s)" as used herein is intended to mean Radio Frequency Identification (RFID) communication, Bluetooth® protocols, Near field Communication (NFC), Near Field Magnetic Inductance Communication (NFMIC), Wi-Fi, LTE, Airdrop® communication, or any other wireless protocol sufficient to communicate with microcontroller 160. Additionally, display 420 is capable of rendering a visible image, e.g., a bar code or QR code, which can be scanned by an external device as a means for transmitting information from dispensing assembly 200. In some embodiments, antenna 164 is part no.: 2450AT42E0100 available from Johanson Technology Inc.; however it should be appreciated that any antenna capable of communication via the above-identified protocols can be used. Ribbon cable 422 is a flexible ribbon-type circuit that is operatively arranged to bend and flex such that electrical current may still flow from microcontroller 160 to display 420. Ribbon cable 422 extends from display 420 and is connected to circuit board 490 at plug 494.

Figure 14:
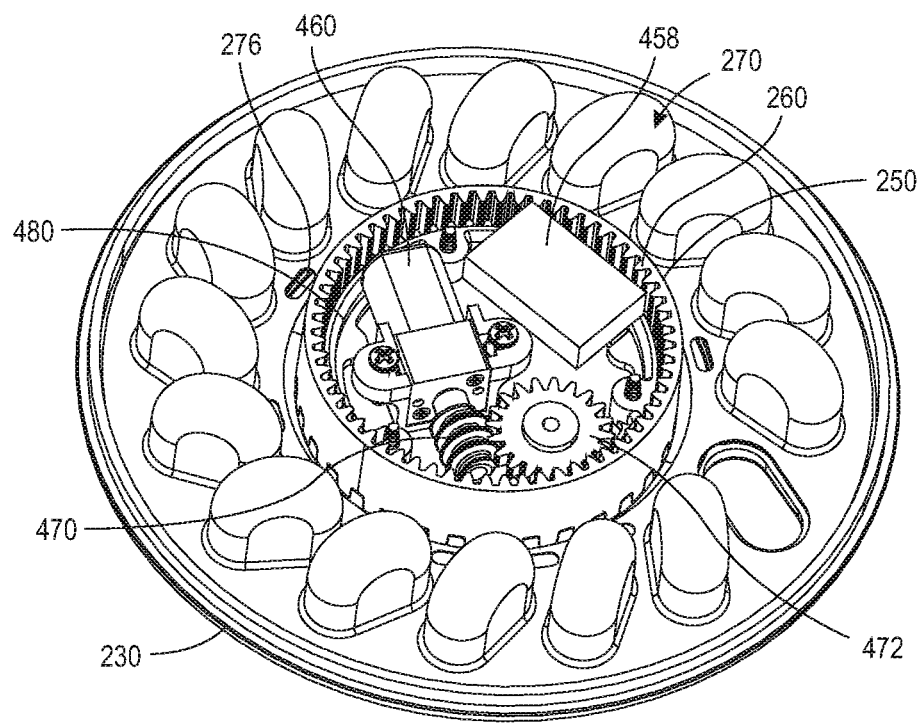
FIG. 14 is a partial top perspective view of the dispensing assembly shown in FIG. 9A.
Figure 15:
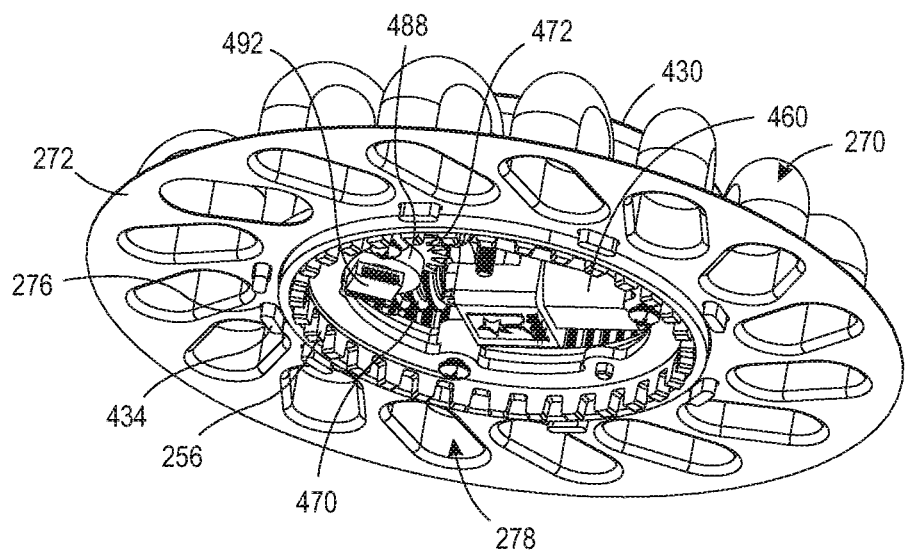
FIG. 15 is a partial bottom perspective view of the dispensing assembly shown in FIG. 9A.

FIG. 14 is a partial top perspective view of dispensing assembly 200. FIG. 15 is a partial bottom perspective view of dispensing assembly 200. The following description is intended to illustrate one potential operation of dispensing assembly 200 and should be read in view of FIGS. 9A-15.

Initially, a user will receive dispensing assembly 200 from the manufacturer, pharmacist, or other healthcare professional. Dispensing assembly 200 will come pre-assembled and closed as illustrated in FIGS. 9A and 9B. In an initial position (i.e., first position), one of compartments 280 is aligned with aperture 222 and aperture 232 and can be depressed such that the tablet arranged therein can be removed from blister pack 270 by the user. Additionally, in the initial position, display 420 indicates that the first tablet aligned with apertures 222 and 232, is available for dispensing. Once the first tablet of the plurality of tablets is dispensed, the user can ingest the tablet. Dispensing assembly 200 may further comprise a dispensing sensor which detects whether a tablet has been removed from its respective compartment 280 of blister pack 270. The timer may reset at the time when the next compartment has aligned with the aperture(s), or at the time when the tablet is dispensed from the compartment, based on the dispensing sensor. Dispensing assembly 200 remains rotationally locked until it is time to take the second tablet of the plurality of tablets. Once the timer determines that it is time to dispense the second tablet, the microcontroller sends a signal to display 420, which displays a prompt indicating to the user that the next tablet is ready to be dispensed. At that time, the microcontroller activates the power between switch 496 and motor 460 allowing the user to activate motor 460 (i.e., switch 496 becomes active). The user can then press switch 496 (by displacing portion 249 of inferior component 230) thereby turning on motor 496. Motor 496 rotates worm drive 470, idler gear 472, drive gear 250, and blister pack 270, with respect to case 202, and remains on until the second compartment of the plurality of compartments 280 is aligned with apertures 222 and 232. Once the second compartment of the plurality of compartments 280 is aligned with apertures 222 and 232, encoder 492 sends a signal to circuit board 490, and the microcontroller turns motor 460 off and resets switch 496 (i.e., motor 460 remains on until encoder 492 registers that a certain angular distance has been travelled by blister pack 270). This operation will be repeated until all of the tablets have been dispensed. In some embodiments, this operation will cease if there is tampering with dispensing assembly 200. Once the blister pack is empty, the user can either dispose of the device, or return it to their healthcare provider for further analysis of usage discussed infra.

It should also be appreciated that the first compartment of blister pack 270 can be left empty, i.e., without a tablet present. This arrangement would be utilized in situations where a patient has been given a first dose of medication via a healthcare provider. In this situation, the healthcare provider or user would then rotate blister pack 270 into the second position by pressing switch 496 and trigger the countdown for the subsequent third position. It should be appreciated that dispensing assembly 200 may communicate with a computer and be programmed as described with reference to FIG. 7.

Figure 16A:
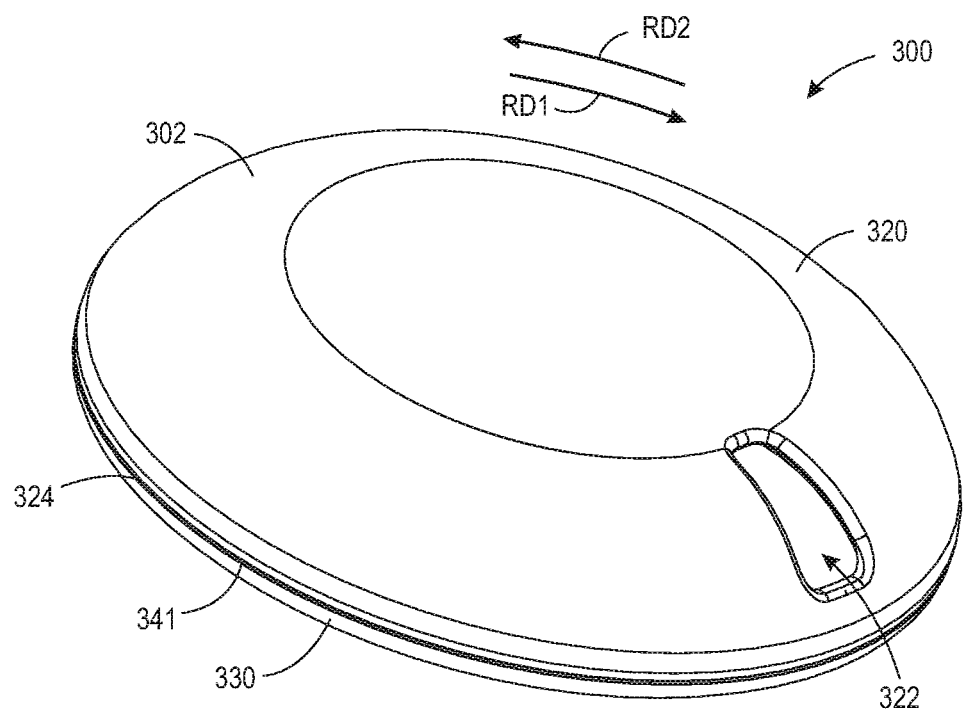
FIG. 16A is a front top perspective view of a dispensing assembly.
Figure 16B:
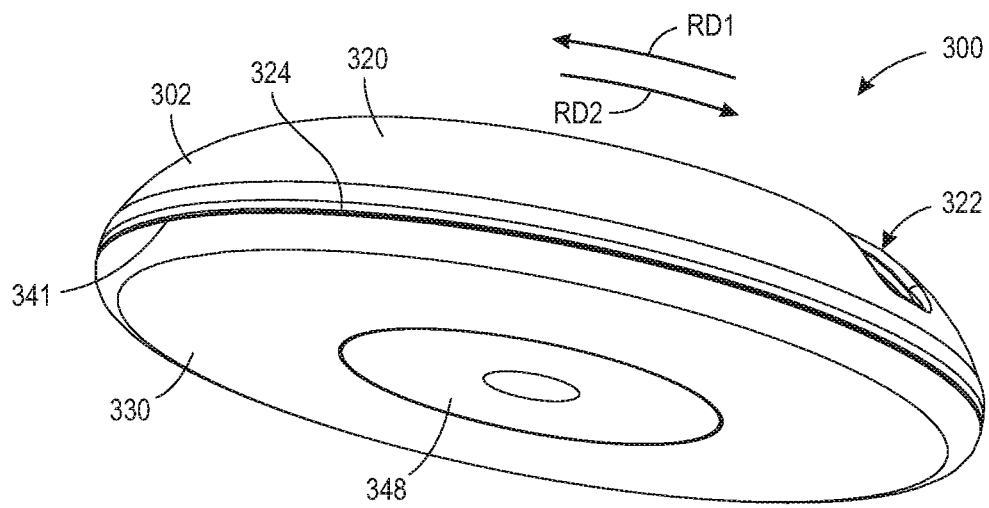
FIG. 16B is a front bottom perspective view of the dispensing assembly shown in FIG. 16A.
Figure 17:
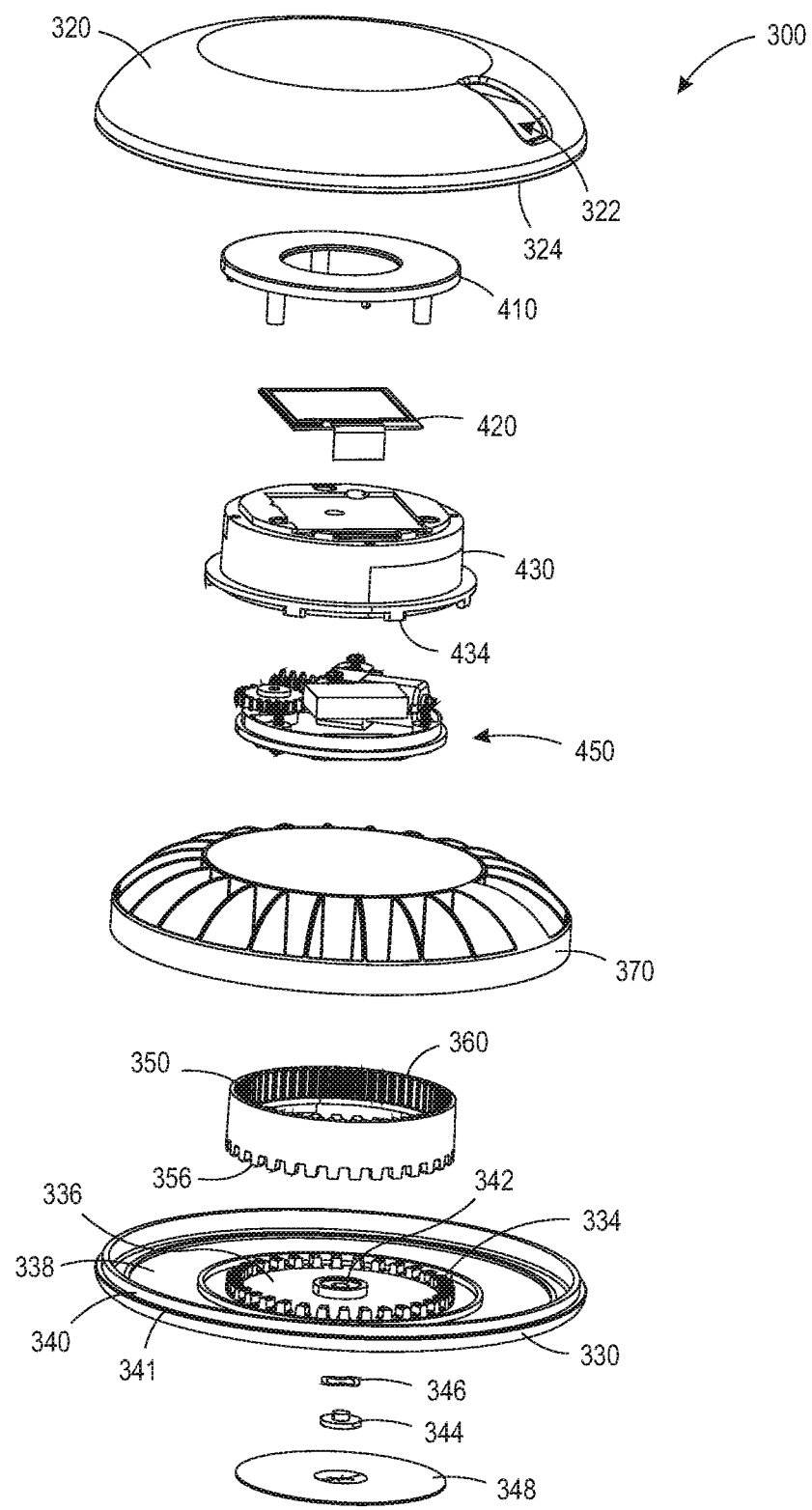
FIG. 17 is a front perspective exploded view of the dispensing assembly shown in FIG. 16A.

FIG. 16A is a front top perspective view of dispensing assembly 300. FIG. 16B is a front bottom perspective view of dispensing assembly 300. FIG. 17 is a front perspective exploded view of dispensing assembly 300. Dispensing assembly 300 generally comprises assembly 304 and assembly 306.

Figure 18A:
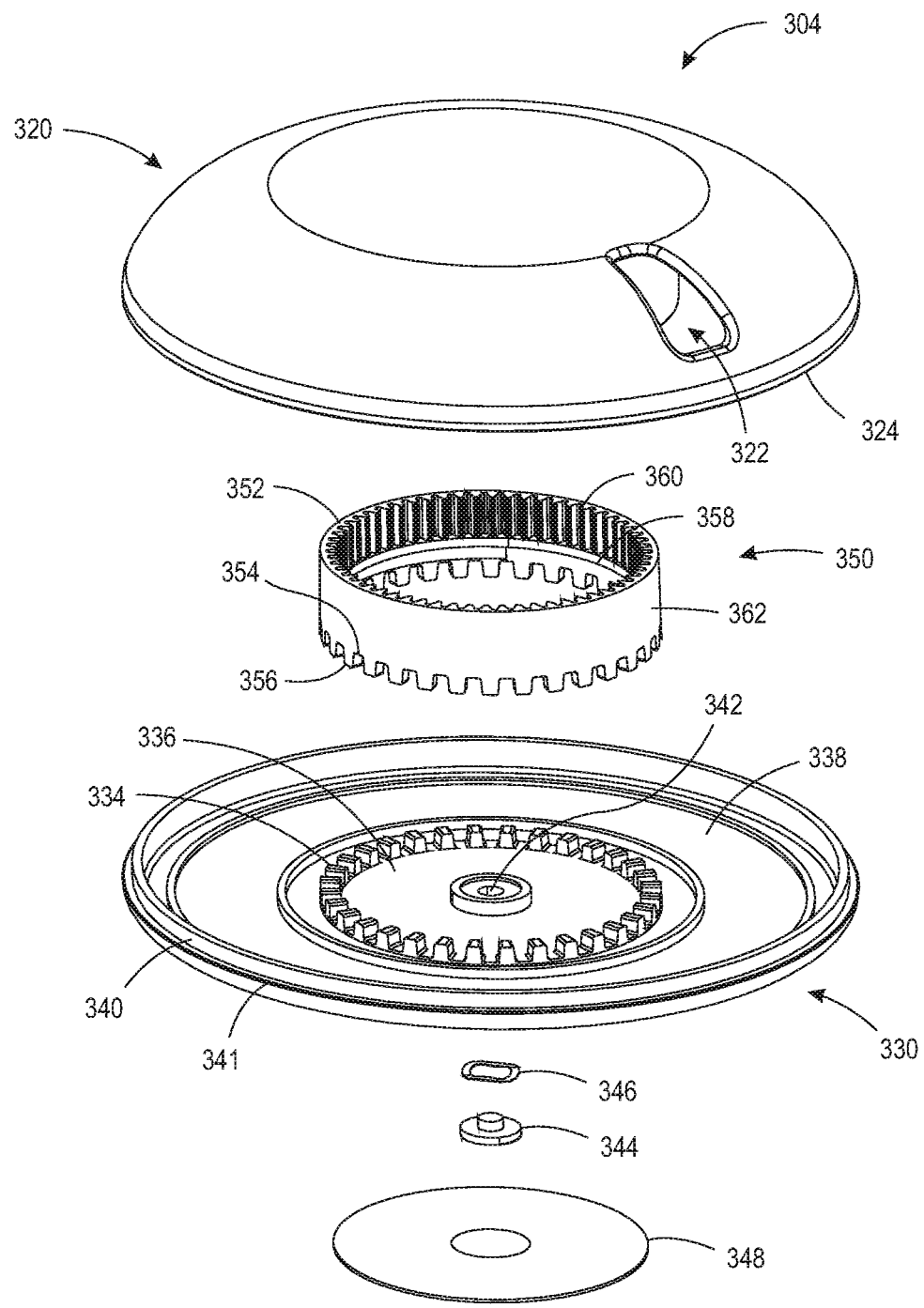
FIG. 18A is a top perspective exploded view of an assembly of the dispensing assembly shown in FIG. 16A.
Figure 18B:
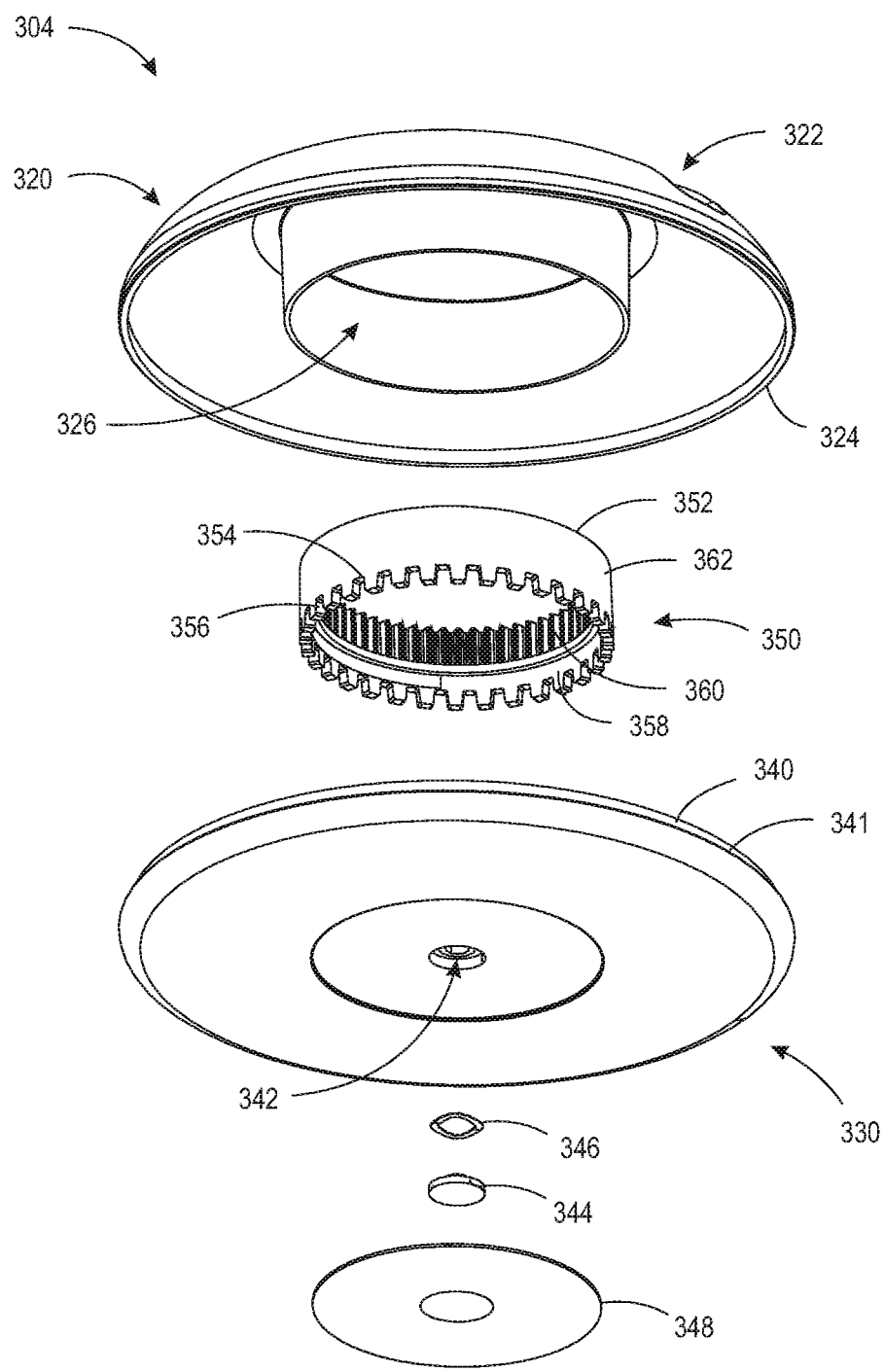
FIG. 18B is a bottom perspective exploded view of the assembly shown in FIG. 18A.

FIG. 18A is a top perspective exploded view of assembly 304 of dispensing assembly 300. FIG. 18B is a bottom perspective exploded view of assembly 304. The following descriptions should be read in view of FIGS. 16A-18B. Assembly 304 generally comprises case 302 and drive gear 350. Case 302 comprises superior component 320, inferior component 330, and cover 348. Case 302 is substantially toroidal in shape and the connection of superior component 320 to inferior component 330 leaves a substantially toroidal cavity therebetween.

Superior component 320 comprises aperture 322, bottom edge 324, and hole 326. Hole 326 is arranged to fit around drive gear 350 and electronics assembly 400, as will be discussed in greater detail below. Inferior component 330 comprises teeth 334, surface 336, surface 338, flange 340 having edge 341, and hole 342. Inferior component 330 is arranged to be non-rotatably connected to superior component 320 and drive gear 350. Specifically, superior component 320 is arranged to non-rotatably connect to flange 340 such that bottom edge 324 abuts against or is arranged substantially proximate to edge 341. Superior component 320 may be connected to inferior component 330 via a press or interference fit. It should be appreciated, however, that any suitable means for non-rotatably connecting superior component 320 to inferior component 330 may be used, such as adhesives, bolts, screws, rivets, nails, welding, etc. In some embodiments, superior component 320 is connected to inferior component 330 such that the only way to disconnect the two components is to destroy case 302. In some embodiments, superior component 320 is connected to inferior component 330 are arranged such that once they are fitted together, no user can open the case, e.g., only a manufacturer or healthcare professional may separate the components. In some embodiments, superior component 320 and inferior component 330 are made of high impact modified Poly(methyl methacrylate) (PMMA); however, it should be appreciated that any other durable material can be used, e.g., high-density polyethylene, low-density polyethylene, metal, high-impact polystyrene, Polycarbonate (PC), Polyether Imide (PEI), or any other material which can resist breaking or cracking while in use, and prevent tampering and/or render evident any tampering caused by the user. As shown, teeth 334 extend from surface 336 and are arranged to engage with teeth 356 of drive gear 350, as will be discussed in greater detail below. Superior component 320 and inferior component 330 are preferably translucent or transparent such that the user can see how many pills or tablets are left therein. In some embodiments, superior component 320 and inferior component 330 are opaque. In some embodiments, only one of the superior component 320 and inferior component 330 is opaque.

Drive gear 350 comprises top surface 352, bottom surface 354 having a plurality of teeth 356, radially inward facing surface 358 having a plurality of teeth 360, and radially outward facing surface 362. Drive gear 350 is arranged to engage inferior component 330. Specifically, teeth 356 engage teeth 334 to non-rotatably connect drive gear 350 to inferior component 330. Teeth 360 are operatively arranged to engage idler gear 472 of motor assembly 450 such that motor 460 rotates electronics assembly 400 relative to drive gear 350 and case 302 (i.e., superior component 320 and inferior component 330), as will be discussed in greater detail below.

Assembly 304 may further comprise plunger 344, spring 346, and/or cover 348. Spring 346 may be arranged in hole 342 or in a counter-bore of hole 342 axially between inferior component 330 and plunger 344. Spring 346 holds plunger 344 above switch 496. Plunger 344 engages hole 342 via a slip or clearance fit. Plunger 344 is operatively arranged to, when displaced by a user, engage switch 496, as will be discussed in greater detail below. In some embodiments, plunger 344 comprises acrylonitrile butadiene styrene (ABS). Cover 348 is generally plate-shaped and may comprise a spherical curvature. Cover 348 is non-rotatably connected to inferior component 330 via any suitable means, such as adhesives, glue, rivets, screws, bolts, nails, welding, etc. Cover 348 comprises portion 349. Portion 349 is elastomeric and may be rounded such that it can be pressed/displaced to engage plunger 344 and/or switch 496 and return to its original shape. In some embodiments, dispensing assembly 300 does not require spring 346 or plunger 344. In such embodiments, portion 349 is displaced and directly engages switch 496. In some embodiments, cover 340 comprises plastic or vinyl.

Figure 19A:
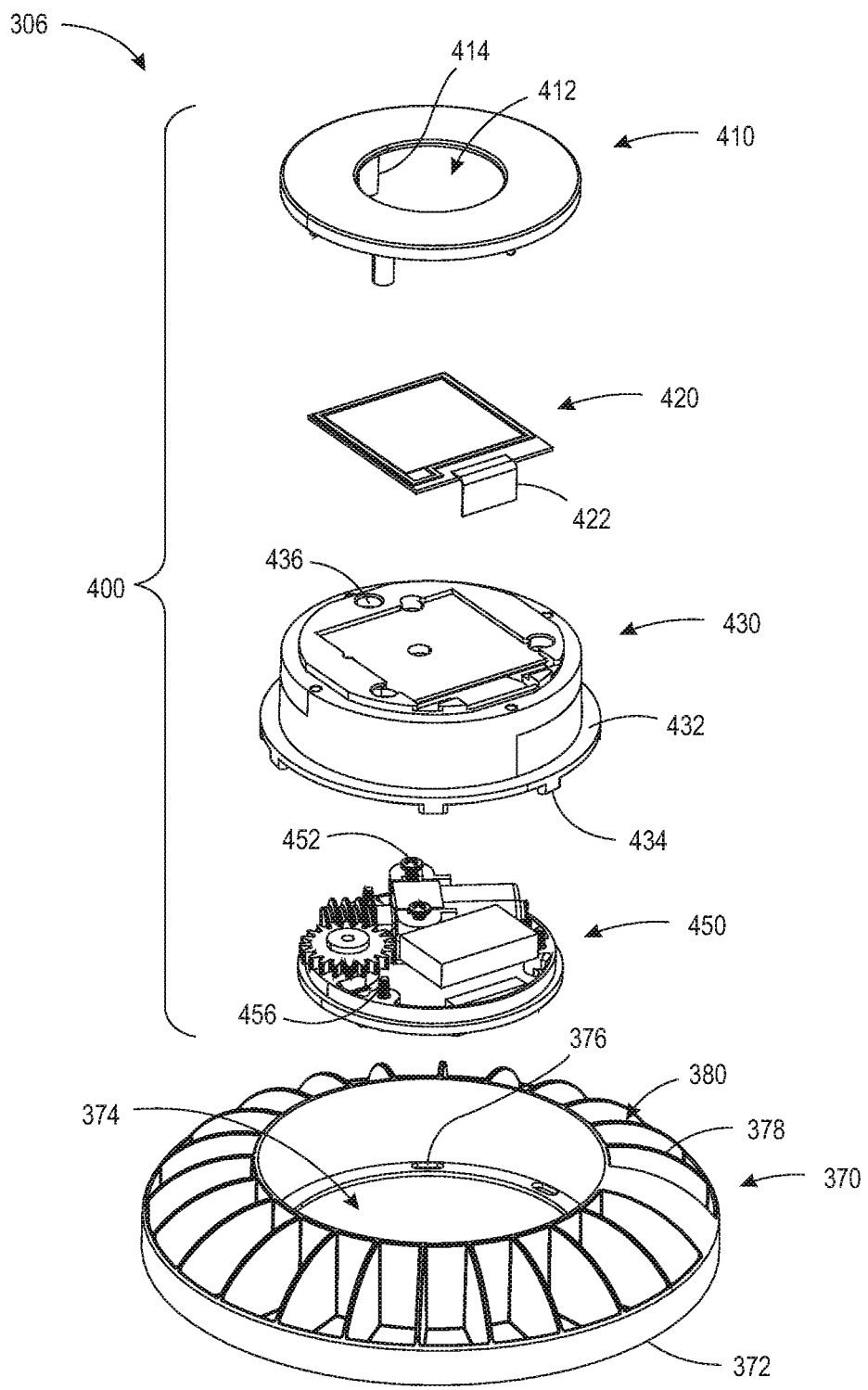
FIG. 19A is a top perspective exploded view of an assembly of the dispensing assembly shown in FIG. 16A.
Figure 19B:
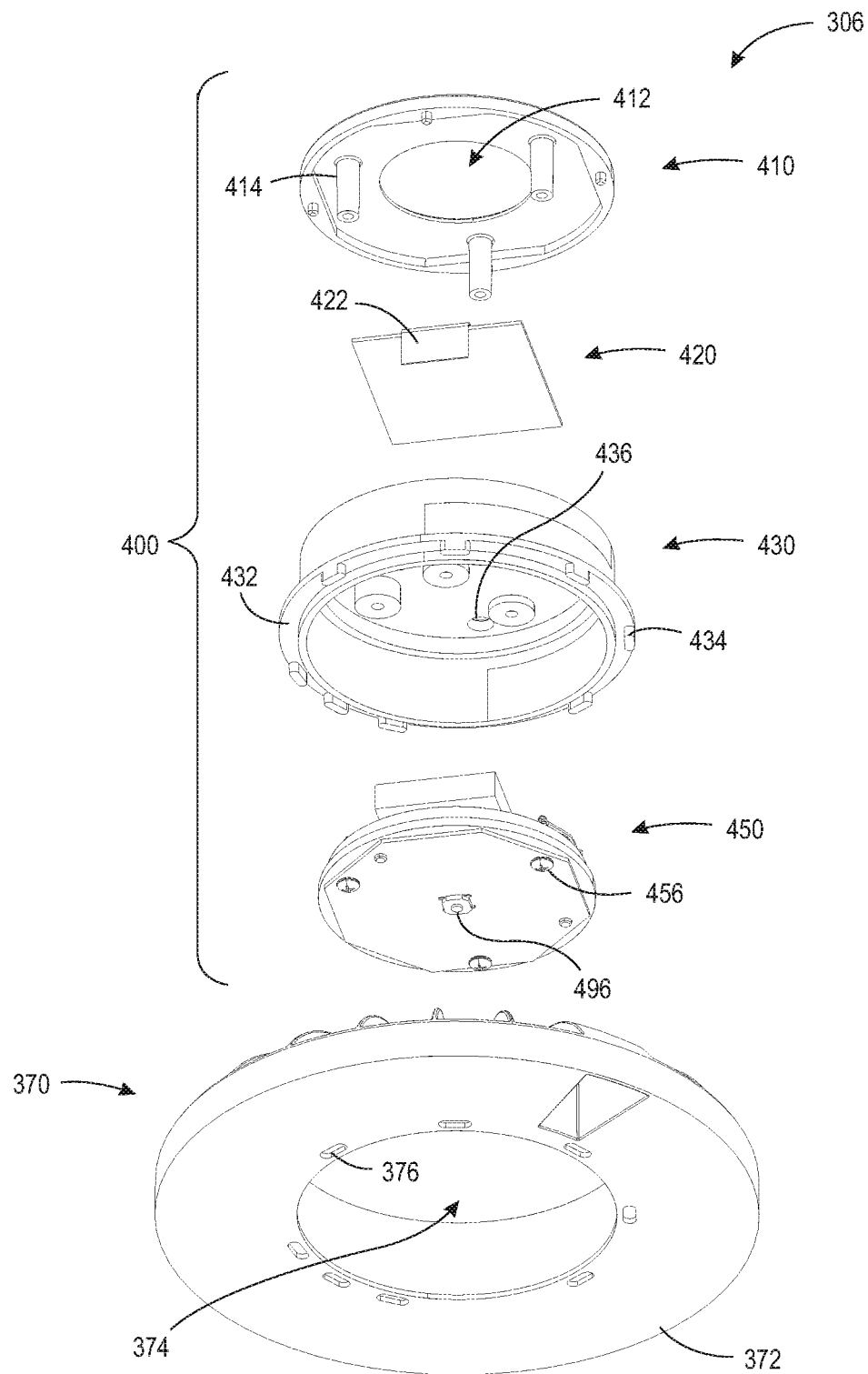
FIG. 19B is a bottom perspective exploded view of the assembly shown in FIG. 19B.

FIG. 19A is a top perspective exploded view of assembly 306 of dispensing assembly 300. FIG. 19B is a bottom perspective exploded view of assembly 306. The following description should be read in view of FIGS. 16A-17 and 19A-B. Assembly 306 generally comprises tray or tablet disc 370 and electronics assembly 400.

Tray 370 is arranged in case 302 and comprises bottom surface 372, through-bore or hole 374, apertures 376, partitions 378, and compartments 380. Tray 370 is rotatably arranged on inferior component 330. Specifically, bottom surface 372 is arranged on surface 338. Compartments 380 are arranged to hold one or more tablets or pills (not shown). As tray 370 is rotated relative to case 302, respective compartments 380 align with aperture 322 such that the user can dump the pill out of the respectively aligned compartment 380 through aperture 322. In some embodiments, compartments 380 are set apart from each other a fixed circumferential distance such that they are evenly spaced. In some embodiments, compartments 380 are set apart from each other a fixed circumferential distance such that they are not evenly spaced. In some embodiments, tray 370 is a prefabricated tray with a plurality of compartments 380 which isolate a single dose of a particular medication, i.e., each tablet is intended to be a single dose of a particular medication. The distance between each tablet or compartment and the size of aperture 322 are proportional such that access to tablets is limited to one tablet at a time through aperture 322. One or more apertures 376 are arranged for engagement with one or more protrusions 434 of housing 430 to non-rotatably connect tray 370 and electronics assembly 400, as will be discussed in greater detail below.

Electronics assembly 400 comprises bezel 410, display 420, housing 430, and motor assembly 450. It should be appreciated that when electronics assembly 400 is fully assembled, bezel 410, display 420, housing 430, and motor assembly 450 are all non-rotatably connected to each other. In some embodiments, when electronics assembly 400 is fully assembled, bezel 410, display 420, housing 430, and motor assembly 450 are all fixedly secured to each other. Bezel 410 comprises hole 412, surface 414, and nuts 416. Bezel is generally a bracket arranged to be fixedly secured to motor assembly 450 via retainer screws 456 and nuts 416, thereby securing display 420 and housing 430 to motor assembly. Nuts 416 project from surface 414, extend through apertures 436, and are threadably engaged with retainer screws 456, as shown. In some embodiments, when bezel 410 is fully connected to motor assembly 450, display and/or housing 430 is axially clamped between surface 414 and motor assembly 450. In some embodiments, bezel 410 further comprises dowels 418 protruding from surface 414. Dowels 418 engage holes 438 to non-rotatably connect bezel 410 and housing 430. Hole 412 allows the user to view display 420 therethrough. Hole 412 is shown as being circular in the figures; however, it should be appreciated that hole 412 may be any geometric shape suitable to view display 420, such as triangular, ovular, ellipsoidal, rectangular, square, trapezoidal, etc.

Display 420 is non-rotatably connected to housing 430 via any suitable means, for example, adhesives, rivets, screws, bolts, nails, welding, soldering, etc. Display 420 is electrically connected to circuit board 490 via cable 422. Cable 422 extends from display 420, through housing 430, and connects to plug 494 of circuit board 490. In some embodiments, cable 422 is a ribbon cable. In some embodiments, display 420 is an E-ink display; however, it should be appreciated that other displays are possible, e.g., a touch-screen display, a Light-Emitting Diode (LED) display, an Electroluminescent (EL) display, a Plasma Display Panel (PDP) display, an Organic Light-Emitting Diode (OLED) display, a Liquid Crystal (LCD) display, or other equivalent displays. One advantage of using an E-ink or electronic paper display is that the time that the next pill will be available will continue to be displayed even though display 420 has been shut down, to avoid unnecessarily draining the batter/power source. Display 420 is arranged to display the current state of dispensing assembly 300 and show the time interval remaining until tray 370 can be rotated to the next position. It should be appreciated that display 420 can be used to display any information deemed important for the prescription of the medication; for example: a prompt to PRESS BUTTON (portion 349) TO START; a prompt TO START PLACE TAG NEAR DEVICE indicating that the user should place the wireless tag near device (as will be discussed in greater detail below); the time that the next pill will be available; the time remaining until the next pill is available; a prompt that NEXT PILL IS READY indicating that the user can press the button (portion 349) to signal dispensing assembly 300 to rotate the pills; a prompt that NEXT PILL IS READY indicating that the user can place the wireless tag near the device to signal dispensing assembly 300 to rotate the pills; a prompt that RX (prescription) IS COMPLETE and/or RETURN TO PHARMACY; a Quick Response (QR) code indicating information about the device, patient, medication, etc.; medication information; prescription information; medication warning information; and, a failure state indicating that dispensing assembly has failed or the prescription has been stopped, which may include a prompt RX STOPPED PLEASE VISIT DOCTOR.

Housing 430 is generally cylindrical and is arranged to encase and protect motor assembly 450 as well as drive gear 350. Housing comprises flange 432 having one or more downward extending protrusions 434. Protrusions 434 are arranged to engage apertures 376 of tray 370 to non-rotatably connect housing 430 and tray 370. Housing 430 further comprises apertures 436, through which nuts 416 extend to connect to retainer screws 456. Apertures 436 may be any geometry suitable for engagement with nuts 416, such as triangular, square, rectangular, circular, ovular, etc. Housing 430 may further comprise holes 438 arranged to engage dowels 418, as previously discussed.

Motor assembly 450 as shown in FIGS. 17, 19A-B, 20, and 21, is substantially similar as motor assembly 450 previously discussed with respect to FIG. 13 and comprises power supply 458, motor 460, worm drive 470, idler gear 472, retainer 480, and circuit board 490. Power supply 458 is intended to be a battery or any combination of multiple batteries that can produce sufficient voltage to power the components of dispensing assembly 300, including motor 460, display 420, encoder 492, circuit board 490, and any other component of dispensing assembly 300 that may require power. Motor 460 is generally an electric motor comprising shaft 464. Motor 460 is mounted to housing 430 via motor mounting screws 452 and motor mounting nuts 454. Worm drive 470 is non-rotatably connected to shaft 464. Motor 460 is arranged to rotate worm drive 470, which is engaged with idler gear 472 to rotate drive gear 350, as will be discussed in greater detail below. Retainer 480 comprises holes 482, slot 484, and hole 486. Idler gear 472 is rotatably connected to retainer 480 via hole 486. A portion of idler gear 472 engages hole 486, and idler gear 472 rotates therein. Circuit board 490 is secured to retainer 480 via retainer screws 456. Specifically, retainer screws 456 extend up through holes 498 and 482, and secure into nuts 416. Circuit board 490 comprises encoder 492, encoder magnet 488, plug 494, and switch 496. When motor assembly 450 is assembled, encoder magnet 488 and encoder 492 are aligned with and positioned under idler gear 472, and plug 494 fits within slot 484.

Encoder 492 is a magnetic encoder which works in conjunction with encoder magnet 488 and idler gear 472 to sense the rotation of idler gear 472. In some embodiments, idler gear 472 comprises a ferrous metal. Idler gear 472 comprises precisely machined teeth that provide a code pattern. As idler gear 472 rotates, these teeth disturb the magnetic flux emitted by encoder magnet 488, causing the flux field to expand and collapse. These changes in the magnetic field are sensed by encoder 492, which generates a corresponding digital or pulse signal output. For example, once idler gear 472 has rotated a predetermined amount (i.e., idler gear 472 has rotated to align the next tablet for removal from dispensing assembly 300), encoder 492 sends a signal to circuit board 490 to stop motor 460. Encoder 492 and encoder magnet 488 may act as a Hall effect device, which senses a change in voltage, or a magnetoresistive device, which senses a change in magnetic field. In some embodiments, encoder 492 and encoder magnet 488 may be replaced by a sensor (e.g., optical sensor) operatively arranged to sense and store the rotational position of idler gear 472, drive gear 250, and/or tray 370. It should be appreciated that electronics assembly 400 may be programed to rotate to align any of the plurality of compartments 380 with aperture 322, not just the "next compartment." For example, each compartment of plurality of compartments 380 is given a label (e.g., compartments A-O), with various medications being arranged therein, and depending on which medication needs to be taken at that time, motor rotates tray 370 to align the desired compartment with aperture 322.

Circuit board 490 may further comprise the same or substantially similar components to that of first circuit 138 as described in reference to FIG. 3. As such, circuit board 490 may further comprise microcontroller 160, timer 162, antenna 164, and sensor 169 (in addition to or in place of encoder 492 and encoder magnet 488 as previously discussed). Microcontroller 160 further includes processor 170 and memory 172, which are operatively arranged to store and execute a set of non-transitory computer readable instructions. Memory 172 can store a first data set comprised of at least one date, at least one time, a rotational position of the tablet disc, and an integer. The date, time, and integer can reflect the history of a user's interaction with dispensing assembly 300 and keep track of which pill/tablet was accessed at what time. In some embodiments, microcontroller 160 is a Cypress Semiconductor part no.: CY8C4247LQI-BL483 available from Mouser Electronics; however, it should be appreciated that any other suitable microcontroller could be used to store the set of non-transitory computer readable instructions and first data set.

Timer 162 is a simple circuit operatively arranged to provide a base time signal to a microcontroller. This circuit comprises, for example, a crystal quartz oscillator. In some embodiments, timer 162 is a crystal oscillator part no.: ECS-240-8-36CKM available from ECS Inc.; however, it should be appreciated that any crystal oscillator that can communicate with microcontroller 160 and keep time can be utilized. Antenna 164 is operatively arranged to communicate with microcontroller 160 and can be utilized to send/receive a wireless signal/communication. It should be appreciated that "wireless communication(s)" as used herein is intended to mean Radio Frequency Identification (RFID) communication, Bluetooth® protocols, Near field Communication (NFC), Near Field Magnetic Inductance Communication (NFMIC), Wi-Fi, LTE, Airdrop® communication, or any other wireless protocol sufficient to communicate with microcontroller 160. Additionally, display 420 is capable of rendering a visible image, e.g., a bar code or QR code, which can be scanned by an external device as a means for transmitting information from dispensing assembly 300. In some embodiments, antenna 164 is part no.: 2450AT42E0100 available from Johanson Technology Inc.; however it should be appreciated that any antenna capable of communication via the above-identified protocols can be used. Ribbon cable 422 is a flexible ribbon-type circuit that is operatively arranged to bend and flex such that electrical current may still flow from microcontroller 160 to display 420. Ribbon cable 422 extends from display 420 and is connected to circuit board 490 at plug 494.

Figure 20:
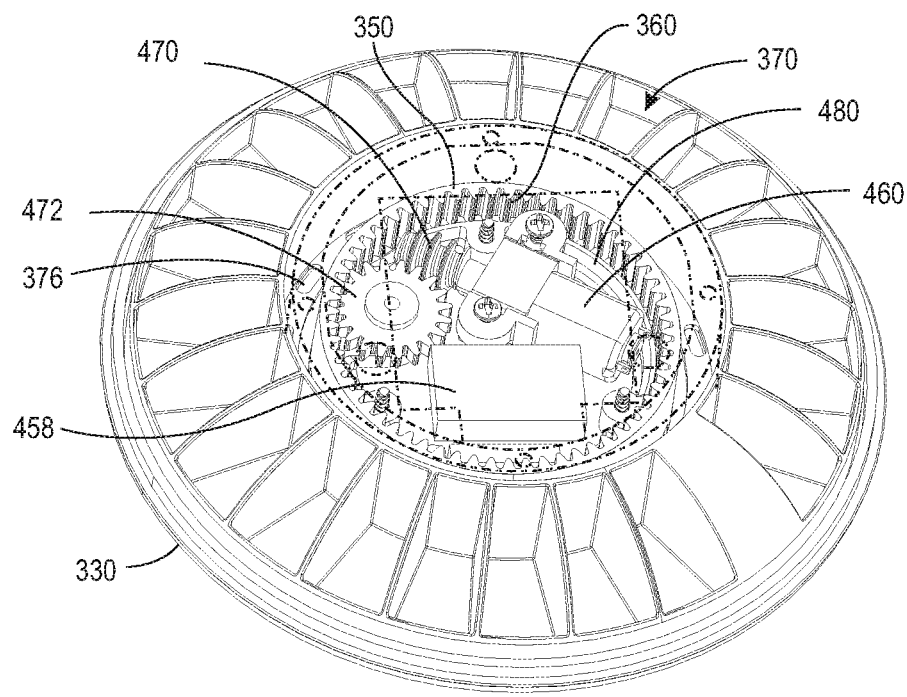
FIG. 20 is a partial top perspective view of the dispensing assembly shown in FIG. 16A; and, FIG. 21 is a partial bottom perspective view of the dispensing assembly shown in FIG. 16A.
Figure 21:
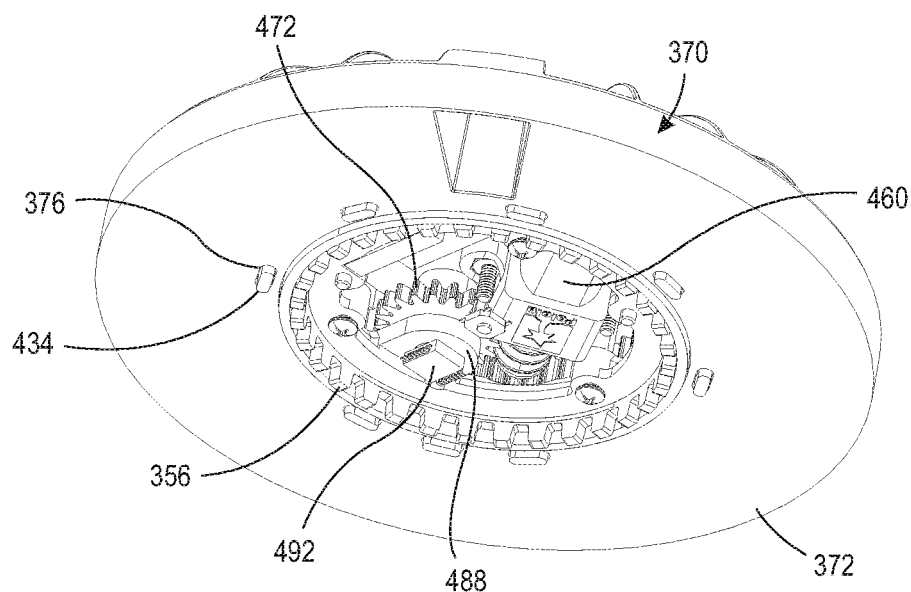

FIG. 20 is a partial top perspective view of dispensing assembly 300. FIG. 21 is a partial bottom perspective view of dispensing assembly 300. The following description is intended to illustrate one potential operation of dispensing assembly 300 and should be read in view of FIGS. 16A-21.

Initially, a user will receive dispensing assembly 300 from the manufacturer, pharmacist, or other healthcare professional. Dispensing assembly 300 will come pre-assembled and closed as illustrated in FIGS. 16A and 16B. In an initial position (i.e., first position), one of compartments 380 is aligned with aperture 322 such that the tablet arranged therein can be removed from tray 370 by the user. Additionally, in the initial position, display 420 indicates that the first tablet aligned with aperture 322 is available for dispensing. Once the first tablet of the plurality of tablets is dispensed, the user can ingest the tablet. Dispensing assembly 300 may further comprise a dispensing sensor which detects whether a tablet has been removed from its respective compartment 380 of tray 370. The timer may reset at the time when the next compartment has aligned with the aperture, or at the time when the tablet is dispensed from the compartment, based on the dispensing sensor. Dispensing assembly 300 remains rotationally locked until it is time to take the second tablet of the plurality of tablets. Once the timer determines that it is time to dispense the second tablet, the microcontroller sends a signal to display 420, which displays a prompt indicating to the user that the next tablet is ready to be dispensed. At that time, the microcontroller activates the power between switch 496 and motor 460 allowing the user to activate motor 460 (i.e., switch 496 becomes active). The user can then press switch 496 (by displacing portion 349 of inferior component 330) thereby turning on motor 496. Motor 496 rotates worm drive 470, idler gear 472, drive gear 250, and blister pack 270, with respect to case 302, and remains on until the second compartment of the plurality of compartments 380 is aligned with aperture 322. Once the second compartment of the plurality of compartments 380 is aligned with aperture 322, encoder 492 sends a signal to circuit board 490, and the microcontroller turns motor 460 off and resets switch 496 (i.e., motor 460 remains on until encoder 492 registers that a certain angular distance has been travelled by tray 370). This operation will be repeated until all of the tablets have been dispensed. In some embodiments, this operation will cease if there is tampering with dispensing assembly 300. Once the tray is empty, the user can either dispose of the device, or return it to their healthcare provider for further analysis of usage discussed infra.

It should also be appreciated that the first compartment of tray 370 can be left empty, i.e., without a tablet present. This arrangement would be utilized in situations where a patient has been given a first dose of medication via a healthcare provider. In this situation, the healthcare provider or user would then rotate tray 370 into the second position by pressing switch 496 and trigger the countdown for the subsequent third position. It should be appreciated that dispensing assembly 300 may communicate with a computer and be programmed as described with reference to FIG. 7.

In some embodiments, dispensing assemblies 100, 200, and 300 comprise a Global Positioning System (GPS) device to capture geolocation data noting where the device was activated and current location data. The GPS device may be operatively arranged to allow geofencing, such that a boundary of use/non-use is created. As such, dispensing assemblies 100, 200, and 300 have the ability to lock-out use if located in an unapproved geolocation. Additionally, the GPS device may be utilized to find a lost dispensing assembly.

In some embodiments, dispensing assemblies 100, 200, and 300 comprise one or more accelerometers to capture rapid movement data (and time stamp of events for evidence). For example, the accelerometer may measure device abuse (e.g., dropped, thrown, beaten or struck, etc.) and store the time of the occurrence. For example, the one or more accelerometers and/or one or more sensors can detect motion to log behavioral events (e.g., breaking in, destroying, etc.), the time and location of which will be logged. Additionally, the accelerometer can sense that the device is in a currently operating vehicle and prevent access to the pills therein during operation of the vehicle.

In some embodiments, dispensing assemblies 100, 200, and 300 can allow for per-pill data capture and mapping "prescription" vs. "real-time" use, or "intended" vs. "actual" use. For example, dispensing assemblies 100, 200, and 300 can be monitored to determine how well the medication is working based on the prescribed drugs compared to how the drugs are actually taken. Dispensing assemblies 100, 200, and 300 can measure and store the exact time that each pill has been taken (e.g., via one or more sensors) and such information is compared to the prescribed schedule to address compliance with how medication is prescribed/taken. Such feature is an extension of efficacy beyond the pharmacist window to actual patient use.

In some embodiments, dispensing assemblies 100, 200, and 300 are arranged to be loaded (i.e., with medication) by the pharmacist, user, doctor, and/or healthcare provider. Such feature enables dispensing assemblies 100, 200, and 300 to be loaded privately by the user (e.g., at home). Furthermore, it should be appreciated that dispensing assemblies 100, 200, and 300 may comprise a smaller and more ergonomically simpler design than other pill dispensers, which allow for easier use by elderly, arthritic, and youth, as well as easier dispensing by pharmacists and healthcare providers.

In some embodiments, dispensing assemblies 100, 200, and 300 are operatively arranged to store all information for future secured upload according to compliance with Health Insurance Portability and Accountability Act (HIPAA). Such data could be used for research purposes to determine just how effective a medication and/or the prescribed schedule of that medication is. Data may be stored on dispensing assemblies 100, 200, and 300 directly or remotely (i.e., cloud), and can be transmitted to a remote location, either in real time or once all of the pills have been dispensed and the device is returned to the pharmacy (i.e., pharmacist can manually scan the device for transfer of stored data).

In some embodiments, dispensing assemblies 100, 200, and 300 may comprise an alarm which alerts the user that it is time to take a pill. Said alarm may be in the form of a sound, an indicator light or screen, a vibration, or any other suitable form of alarm.

In some embodiments, dispensing assemblies 100, 200, and 300 may further comprise a cellular chip such that the device may be used to call the patient/pharmacist/doctor. For example, if a dosage has been missed, the nurse/doctor can contact the patient by "calling" the device. This cellular chip may allow for open line or two-way communication (i.e., similar to OnStar® communication system). Dispensing assemblies 100, 200, and 300 may further comprise a speaker and a microphone to implement such communication system.

In some embodiments, dispensing assemblies 100, 200, and 300 are capable of being modified on a "per pill" basis. If a dosage is missed or not taken on time, the prescription may be either manually or automatically modified. For example, if a pill is taken 3 hours late, the device will lock out and add additional time before the subsequent pill will become available. Because dispensing assemblies 100, 200, and 300 are capable of detecting non-compliance (i.e., prescribed use vs. actual use), circuit board 490 can be programed with an algorithm that changes the time of the next pill to get the prescription schedule back on track (i.e., automatic modification).

In some embodiments, dispensing assemblies 100, 200, and 300 comprise communication capability such that the prescription schedule can be modified remotely by a doctor (i.e., manual modification).

In some embodiments, repeated non-compliance shuts off further access to pills. Non-compliance detection may be communicated on display 420, such that display 420 displays a prompt indicating that the next pill time has been changed due to non-compliance or to contact the doctor to reset due to continued non-compliance.

In some embodiments, dispensing assemblies 100, 200, and 300 comprise an integrated biometric scanner (e.g., fingerprint, heart rate, pulse, blood oxygen level, facial recognition, etc.). For example, dispensing assemblies 100, 200, and 300 may comprise two metal tabs that the user's thumbs are placed on to check hear rate. The biometric scanner can be used to access the pills (i.e., make sure the user is the intended user), as well as to measure the user's vitals prior to taking medication (i.e., if heart rate or blood pressure is too high the device may lock out user from taking medication). The prescription schedule may be automatically (i.e., via preprogrammed algorithm) or manually modified based on biometric feedback.

In some embodiments, dispensing assemblies 100, 200, and 300 may further comprise an additional cap that must be defeated to gain access to pills (e.g., a child proof cap).

In some embodiments, dispensing assemblies 100, 200, and 300 are operatively arranged to interact with an identification card or device for activation of the motor to advance the next pill. An identification card or device (e.g., a Near-Field Communication (NFC) device, key fob, magnet, Radio Frequency Identification (RFID), etc.) may be used to prompt dispensing assemblies 100, 200, and 300 to access the next pill. Such device would be in addition to or in place of switch 496 and, when the next pill is available, can be placed at a location proximate to the device to activate motor 460. For example, dispensing assemblies 100, 200, and 300 may prompt the user, via the display, to advance the device to access the next pill. User may then be notified that an identification must be validated, which may be done by placing the identification card proximate the device to wirelessly authenticate the user. When identification is validated, the device advances to the next pill as per the regimented prescriptions. This two-step process, i.e., 1) the device timer approves access to the next pill, and 2) the user is authenticated, the next tablet is maneuvered for access, may be utilized for child protection and to prevent unauthorized access.

In some embodiments, dispensing assemblies 100, 200, and 300 may further comprise an ambulatory connected dispenser system, which allows a user to contact the doctor and request an immediate change to medication access. With the approval from the doctor, a signal is sent to the device that immediately updates the protocol to address the user's need.

It should be appreciated that any of the various components of dispensing assemblies 100, 200, and 300 may be reused after a prescription has been completed.

In some embodiments, dispensing assemblies 100, 200, and 300 can synchronize with Internet System for Tracking Over-Prescribing Act (ISTOP) Prescription Monitoring Program (PMP), the data including the date the prescription was written and dispensed, the drug name and dose/quantity, the days the drug is supplied, the prescriber's name, the prescription interval, the number of times the prescription has been filled, the length of time the user needs access to the device, etc. In some embodiments, dispensing assemblies communicate with each other such that as a first dispensing assembly is fully emptied, it communicates with a second dispensing assembly to activate.

In some embodiments, dispensing assemblies 100, 200, and 300 further comprise a "pill kill" feature such that the pills arranged therein can be broken down and the contents made useless. For example, dispensing assemblies 100, 200, and 300 may be modified with one or more tubes that allow a small amount of gas or fluid activated by a chip to impregnate each container to destroy the pills therein.

It will be appreciated that various aspects of the disclosure above and other features and functions, or alternatives thereof, may be desirably combined into many other different systems or applications. Various presently unforeseen or unanticipated alternatives, modifications, variations, or improvements therein may be subsequently made by those skilled in the art which are also intended to be encompassed by the following claims.

LIST OF REFERENCE NUMERALS

100 Dispensing assembly
102 Case
104 Superior component
106 Inferior component
108 First cavity
110 First aperture
112 Second aperture
114 First rim
116 First plurality of teeth
118 Opening
120 Second rim
122 Tablet disc
124 Plurality of tablets
126 First through-bore
128 Second through-bore
130 Lock
132 First component
134 Second component
136 Display
138 First circuit
140 First projection
142 First surface
144 Second cavity
146 Second projection
148 Second surface
150 Plurality of grips
152 Solenoid actuator
154 Pivotable catch
156 Second plurality of teeth
158 Ratchet
160 Microcontroller
162 Timer
164 Antenna
166 Power supply
168 Flex circuit
169 Sensor
170 Processor
172 Memory
174 First computer
176 Initial position
178 Second position
180 Software interface
182 First medication
184 List
186 Graph
188 First time interval
190 Second time interval
200 Dispensing assembly
202 Case
204 Assembly
206 Assembly
220 Superior component
222 Aperture
224 Bottom Edge
230 Inferior component
232 Aperture
234 Teeth
236 Surface
238 Surface
240 Flange
241 Edge
242 Hole
244 Plunger
246 Spring
248 Cover
249 Portion
250 Drive gear
252 Top surface
254 Bottom surface
256 Teeth
258 Radially inward facing surface
260 Teeth
262 Radially outward facing surface
270 Blister pack (or tablet disc)
272 Disc
274 Through-bore
276 Apertures
278 Apertures
280 Compartments
300 Dispensing assembly
302 Case
304 Assembly
306 Assembly
320 Superior component
322 Aperture
324 Bottom Edge
330 Inferior component
334 Teeth
336 Surface
338 Surface
340 Flange
341 Edge
342 Through-bore
344 Plunger
346 Spring
348 Cover
349 Portion
350 Drive gear
352 Top surface
354 Bottom surface
356 Teeth
358 Radially inward facing surface
360 Teeth
362 Radially outward facing surface
370 Tray (or tablet disc)
372 Bottom surface
374 Through-bore
376 Apertures
378 Partitions
380 Compartments
400 Electronics assembly
410 Bezel
412 Hole
414 Surface
416 Nuts
418 Dowels 420 Display
422 Ribbon cable
430 Housing
432 Flange
434 Protrusions
436 Apertures
438 Holes
450 Motor assembly
452 Motor mounting screws
454 Motor mounting nuts
456 Retainer screws
458 Power supply
460 Motor
462 Holes
464 Shaft
470 Worm drive
472 Idler gear
480 Retainer
482 Holes
484 Slot
486 Hole
488 Encoder magnet
490 Circuit board
492 Encoder
494 Plug
496 Switch
498 Holes
DR1 Direction
DR2 Direction
RD1 Rotational direction
RD2 Rotational direction

What is claimed is:

1. A dispensing assembly, comprising:
 a case including at least one aperture;
  a superior component including the at least one aperture;
  an inferior component non-rotatably connected to the superior component, the inferior component including:
   a first surface;
   a first plurality of teeth extending from the first surface; and,
   a first hole; and,
  a cavity formed between the superior component and inferior component;
 a drive gear operatively arranged to engage the case, wherein the drive gear comprises a second plurality of teeth operatively arranged to engage the first plurality of teeth;
 a tablet disc rotatably arranged in the case and including a plurality of compartments; and,
 an electronics assembly, including:
  a motor engaged with the drive gear; and,
  a housing operatively arranged to engage the tablet disc;
 wherein:
  the drive gear, the tablet disc, and the electronics assembly are arranged within the cavity; and,
  the motor is arranged to rotate the electronics assembly and the tablet disc with respect to the case to align the plurality of compartments with the at least one aperture.

2. The dispensing assembly as recited in claim 1, wherein the electronics assembly further comprises:
 a worm drive non-rotatably connected to the motor; and,
 an idler gear engaged with the worm drive and the drive gear.

3. The dispensing assembly as recited in claim 2, wherein the electronics assembly further comprises a circuit board operatively arranged to control the motor.

4. The dispensing assembly as recited in claim 3, wherein the electronics assembly further comprises a display electrically connected to the circuit board.

5. The dispensing assembly as recited in claim 3, wherein the electronics assembly further comprises a sensor operatively arranged to detect a displaced angular distance of the tablet disc.

6. The dispensing assembly as recited in claim 5, wherein the sensor comprises a magnetic encoder.

7. The dispensing assembly as recited in claim 1, wherein the electronics assembly further comprises a sensor operatively arranged to in conjunction with a microcontroller, turn off the motor when the displaced angular distance is equal to a predetermined angular distance.

8. The dispensing assembly as recited in claim 1, wherein the at least one aperture comprises a first aperture arranged on the superior component and a second aperture arranged on the inferior component, the first and second apertures being aligned.

9. The dispensing assembly as recited in claim 1, wherein the drive gear comprises a third plurality of teeth engaged with the idler gear.

10. The dispensing assembly as recited in claim 1, wherein the electronics assembly further comprises a switch connected to the circuit board, wherein the switch is operatively arranged to activate the motor.

11. The dispensing assembly as recited in claim 10, wherein the switch can be activated through the first hole.

12. A dispensing assembly, comprising:
 a case including:
  a superior component including at least one aperture;
  an inferior component non-rotatably connected to the superior component, the inferior component comprising a first surface, a first plurality of teeth extending from the first surface, and a first hole, wherein a cavity is formed between the superior component and the inferior component;
 a drive gear operatively arranged to engage the case;
 a tablet disc rotatably arranged in the case and including a plurality of compartments; and,
 an electronics assembly, including:
  a motor engaged with the drive gear; and,
  a housing operatively arranged to engage the tablet disc;
 wherein:
  the motor is arranged to rotate the electronics assembly and the tablet disc with respect to the case to align the plurality of compartments with the at least one aperture; and,
  the drive gear, the tablet disc, and the electronics assembly are arranged within the cavity.

13. The dispensing assembly as recited in claim 12, wherein the electronics assembly further comprises:
 a worm drive non-rotatably connected to the motor; and,
 an idler gear engaged with the worm drive and the drive gear.

14. The dispensing assembly as recited in claim 13, wherein the drive gear comprises a third plurality of teeth engaged with the idler gear.

15. The dispensing assembly as recited in claim 13, wherein the electronics assembly further comprises a switch connected to the circuit board, wherein the switch is operatively arranged to activate the motor.

16. The dispensing assembly as recited in claim 12, wherein the electronics assembly further comprises a circuit board operatively arranged to control the motor.

17. The dispensing assembly as recited in claim 16, wherein the electronics assembly further comprises a sensor operatively arranged to detect a displaced angular distance of the tablet disc.

18. The dispensing assembly as recited in claim 12, wherein the drive gear comprises a second plurality of teeth operatively arranged to engage the first plurality of teeth.

* * * * *